United States Patent
Moench

(10) Patent No.: US 9,155,873 B2
(45) Date of Patent: Oct. 13, 2015

(54) REUSABLE INTRAVAGINAL DELIVERY DEVICE, SYSTEM, AND METHOD

(75) Inventor: Thomas R. Moench, Baltimore, MD (US)

(73) Assignee: ReProtect, Inc., Baltimore, MD (US)

(*) Notice: Subject to any disclaimer, the term of this patent is extended or adjusted under 35 U.S.C. 154(b) by 660 days.

(21) Appl. No.: 13/473,075

(22) Filed: May 16, 2012

(65) Prior Publication Data

US 2012/0296315 A1 Nov. 22, 2012

Related U.S. Application Data

(60) Provisional application No. 61/487,040, filed on May 17, 2011.

(51) Int. Cl.
| | |
|---|---|
| A61F 6/06 | (2006.01) |
| A61F 6/14 | (2006.01) |
| A61F 13/00 | (2006.01) |
| A61M 31/00 | (2006.01) |
| A61K 9/00 | (2006.01) |
| A61K 31/19 | (2006.01) |
| A61K 31/505 | (2006.01) |

(52) U.S. Cl.
CPC ............ *A61M 31/002* (2013.01); *A61K 9/0036* (2013.01); *A61K 31/19* (2013.01); *A61K 31/505* (2013.01); *A61M 2210/1475* (2013.01)

(58) Field of Classification Search
None
See application file for complete search history.

(56) References Cited

U.S. PATENT DOCUMENTS

| | | | |
|---|---|---|---|
| 4,228,797 A | 10/1980 | Dickey | |
| 4,311,543 A | 1/1982 | Strickman et al. | |
| 4,393,871 A * | 7/1983 | Vorhauer et al. | 128/833 |
| 4,693,705 A | 9/1987 | Gero | |
| 4,959,216 A | 9/1990 | Daunter | |
| 5,044,376 A * | 9/1991 | Shields | 128/837 |
| 5,295,984 A | 3/1994 | Contente et al. | |
| 5,516,495 A | 5/1996 | Kutner et al. | |
| 5,592,949 A * | 1/1997 | Moench et al. | 128/837 |
| 5,617,877 A * | 4/1997 | Moench et al. | 128/837 |
| 5,702,711 A | 12/1997 | Parab | |
| 5,928,195 A | 7/1999 | Malamud et al. | |
| 6,180,129 B1 | 1/2001 | Magruder et al. | |
| 6,416,779 B1 | 7/2002 | D'Augustine et al. | |

(Continued)

FOREIGN PATENT DOCUMENTS

| | | |
|---|---|---|
| DE | 2721014 A1 | 11/1978 |
| EP | 0710480 A | 5/1996 |

(Continued)

OTHER PUBLICATIONS

NPL search string (Google 1); downloaded May 21, 2015.*

(Continued)

*Primary Examiner* — Jeffrey T Palenik
(74) *Attorney, Agent, or Firm* — Whyte Hirschboeck Dudek S.C.

(57) ABSTRACT

The present disclosure is directed to a system, device and methods for treating or preventing genital tract infection. The system includes a point-of-use recharge kit having a first reusable intravaginal delivery device (RIDD1) and a second reusable intravaginal delivery device (RIDD2), and a therapeutic agent. Each RIDD includes a permeable wall defining an enclosed interior reservoir. The reservoir is adapted to receive the therapeutic agent. The system enables the point-of-use loading and reloading at least one of the RIDDs with the therapeutic agent by the end user.

20 Claims, 9 Drawing Sheets

(56) References Cited

U.S. PATENT DOCUMENTS

| | | | |
|---|---|---|---|
| 6,982,091 | B2 | 1/2006 | Pauletti et al. |
| 7,622,530 | B2 | 11/2009 | Pinchuk et al. |
| 7,768,909 | B1 | 8/2010 | Parlamas et al. |
| 7,858,110 | B2 | 12/2010 | Kuzma et al. |
| 7,914,806 | B2 | 3/2011 | Strickler et al. |
| 2004/0043071 | A1 | 3/2004 | Pauletti et al. |
| 2004/0110721 | A1 | 6/2004 | Zeng |
| 2006/0002966 | A1 | 1/2006 | Pauletti et al. |
| 2006/0105008 | A1 | 5/2006 | Ahmad et al. |
| 2007/0043332 | A1 | 2/2007 | Malcolm et al. |
| 2008/0138379 | A1 | 6/2008 | Jennings-Spring |
| 2009/0214474 | A1 | 8/2009 | Jennings |
| 2009/0291120 | A1 | 11/2009 | Tuominen et al. |
| 2011/0008293 | A1 | 1/2011 | Bhandari |
| 2011/0020265 | A1 | 1/2011 | Batcheller et al. |
| 2012/0070476 | A1* | 3/2012 | Moench et al. ............... 424/400 |

FOREIGN PATENT DOCUMENTS

| | | | | |
|---|---|---|---|---|
| EP | 1481666 | A1 | 12/2004 | |
| EP | 2062568 | A1 | 5/2009 | |
| WO | WO 94/08536 | * | 4/1994 | ............... A61F 6/06 |
| WO | 03000224 | A | 1/2003 | |
| WO | 2004029125 | A1 | 4/2004 | |
| WO | 2007119185 | A2 | 10/2007 | |
| WO | 2009109966 | A1 | 9/2009 | |
| WO | 2010138823 | A1 | 12/2010 | |
| WO | WO 2010/138823 | A1 * | 12/2010 | ............. A61K 31/19 |

OTHER PUBLICATIONS

NPL search string (Google 2); downloaded May 21, 2015.*
Notification of Transmittal of International Search Report and Written Opinion of the International Searching Authority; International Application No. PCT/US2009/045706; Jul. 31, 2009; 15 pages.
Notification of Transmittal of International Search Report and Written Opinion of the International Searching Authority; International Application No. PCT/US2010/036589; Sep. 24, 2010; 13 pages.
Notification Concerning Transmittal of International Preliminary Report on Patentability; International Application No. PCT/2010/036589; Dec. 8, 2011; 7 pages.
Notification of International Search Report and Written Opinion of the International Searching Authority; International Application No. PCT/US2012/038114; Aug. 9, 2012; 9 pages.

* cited by examiner

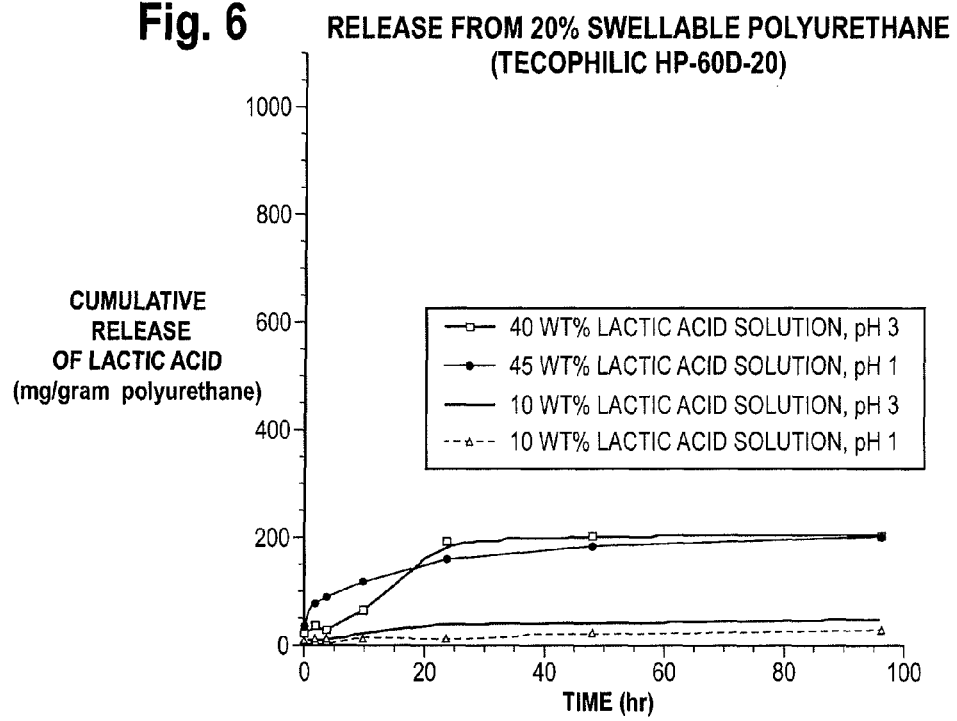
Fig. 6 RELEASE FROM 20% SWELLABLE POLYURETHANE (TECOPHILIC HP-60D-20)
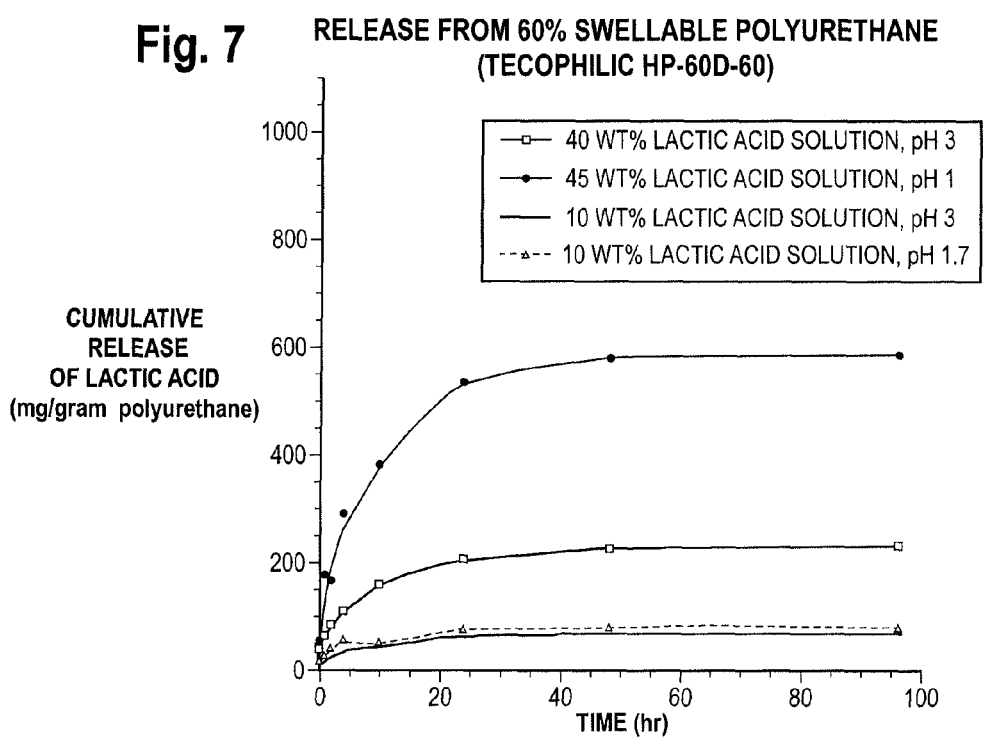
Fig. 7 RELEASE FROM 60% SWELLABLE POLYURETHANE (TECOPHILIC HP-60D-60)

REUSABLE INTRAVAGINAL DELIVERY DEVICE, SYSTEM, AND METHOD

PRIORITY CLAIM

This application claims priority to U.S. Provisional Ser. No. 61/487,040 filed on 17 May 2011, the entire content of which is incorporated by reference herein.

BACKGROUND

The disclosure is directed to a system, device and methods for the treatment of genital tract infection.

Genital tract infection is a common and significant health problem for both women and men. Genital tract infection typically falls into one of three categories: endogenous infection, iatrogenic infection, and sexually transmitted infection (STI). Endogenous infection includes bacterial vaginosis and candidiasis, which result from an overgrowth of organisms that are normally present in the vagina. Despite known treatments for endogenous infection, endogenous infections are problematic because they have a high recurrence rate.

Iatrogenic infections represent another type of genital tract infection. Iatrogenic infection occurs when the infectious agent (a bacterium or other micro-organism) is introduced into the reproductive tract through various routes such as menstrual regulation, induced abortion, IUD insertion and/or parturition. Another type of genital tract infection is STI caused by microorganisms that are transmitted through sexual activity with an infected partner. Among the STIs there are several serious diseases such as HIV, Chlamydia trachomatis, human papillomavirus infection with cancerous and non-cancerous epithelial transformation (condyloma and cervical cancer), syphilis and gonorrhea. STIs can affect both men and women, and transmission from infected mother to child during pregnancy is also known.

Bacterial vaginosis (BV) is a frequent endogenous infection and also one of the most common medical conditions of the female genital tract. BV is linked to increased complication in pregnancy, poor birth outcomes including prematurity and systemic infection of the mother and newborn, and may be involved in the pathogenesis of pelvic inflammatory disease and women's risk of acquiring HIV and other STIs. Many questions remain about the etiology of BV, which complicates the management of recurrent infections.

BV is an overgrowth of anaerobic bacteria and a lack of normal Lactobacilli flora, which results in the imbalance of normal vaginal flora. During pregnancy BV is associated with poor perinatal outcome and a cause of preterm birth. Identification and treatment of BV may reduce the risk of such consequences.

Lactic acid, by way of release from an intravaginal delivery device (IDD), is a known treatment for BV. This treatment delivers lactic acid so as to mimic the natural acidic pH of the human vagina. Unfortunately, women who are susceptible to BV often experience frequent relapse and remissions of the condition. The art recognizes the high rate of recurrent BV even after successful episodic treatment.

Treatment of BV with lactic acid is difficult because effective BV treatment requires delivery of not only (i) a sustained amount of lactic acid but also (ii) a large amount of lactic acid into the vaginal cavity. Consequently, episodic treatment of BV is typically unsuccessful over the long term. Conventional IDDs are lacking because a typical IDD cannot keep pace with the natural rate of loss of lactic acid via diffusion through the vaginal epithelium. In particular, conventional IDDs cannot replenish lactic acid to the vaginal lumen at a rate fast enough and for long enough duration to keep pace with this transepithelial flux.

The art recognizes the need for a genital tract treatment regime that can provide both (i) a sustained amount and (ii) a large amount of a therapeutic agent to the genital tract over a long period of time. A need further exists for an intravaginal treatment of BV that can provide a sustained amount and a large amount of lactic acid for a greater time duration than is possible with a conventional IDD alone.

SUMMARY

The present disclosure is directed to a system, device and methods for treating or preventing genital tract infection. The present disclosure utilizes the point-of-use as a parameter by which improved genital tract treatment is delivered. The present disclosure provides the end user with the elements necessary for easy-use, repeated, reliable, and consistent self-administration of a therapeutically effective amount of a therapeutic agent to the genital tract. This point-of-use characteristic embodied in the present disclosure provides a genital tract treatment system with a reliability and efficacy heretofore unforeseen. In some embodiments, the present system, device and methods facilitate end user activity (vis-à-vis equipment availability and ease-of-use) for an improved and extended genital tract treatment protocol that reliably and consistently delivers therapeutically effective amounts of therapeutic agent to the genital tract over extended time durations of a day, a week, a month, six months, a year, two years, or more.

By making self-administration easily repeatable, affordable, and accessible for the end user, the present disclosure provides a genital tract treatment regime that provides markedly improved efficacy and reduction in BV relapse in particular.

The present disclosure provides a system. In an embodiment, a point-of-use load intravaginal delivery system is provided. The system includes a first reusable intravaginal delivery device (RIDD1) and a second reusable intravaginal delivery device (RIDD2). Each RIDD includes a permeable wall defining an enclosed interior reservoir. The reservoir is adapted to receive a therapeutic agent. The system further includes a point-of-use recharge kit containing a therapeutic agent and optionally a recharge vessel and cleaning equipment. The point-of-use (POU) recharge kit is for point-of-use loading and reloading at least one of the RIDDs with the therapeutic agent.

The present disclosure provides a method. In an embodiment, a method for delivering a therapeutic agent to a vagina is provided. The method includes providing a point-of-use recharge kit including a first reusable intravaginal delivery device (RIDD1), a second RIDD (RIDD2) and a therapeutic agent. Each RIDD includes a permeable wall defining an enclosed interior reservoir. Each RIDD is adapted to receive a therapeutic agent. The point-of-use recharge kit optionally includes a recharge vessel and cleaning equipment. The method includes enabling, with the kit, point-of-use loading and reloading of the therapeutic agent to at least one RIDD.

The present disclosure provides another method. In an embodiment, a method for delivering a therapeutic agent to a vagina is provided. The method includes point-of-use loading a first reusable intravaginal delivery device (RIDD1) with a therapeutic agent and inserting the loaded RIDD1 into the vagina. RIDD1 delivers a therapeutically effective amount of the therapeutic agent to the vagina. The method further includes point-of-use loading a second RIDD (RIDD2) with the therapeutic agent. The method includes replacing RIDD1 with RIDD2 in the vagina. RIDD2 delivers a therapeutically effective amount of the therapeutic agent to the vagina.

The present disclosure provides another method. In an embodiment, a method for treating bacterial vaginosis (BV) is provided. The method includes inserting a POU-loaded RIDD1 into the vagina. RIDD1 is POU-loaded with a lactic acid composition. The method includes delivering, with RIDD1, a therapeutically effective amount of the lactic acid composition to the vagina and maintaining vaginal pH at or below 4.5. The method further includes POU-loading RIDD2 with the lactic acid composition. The method includes replacing RIDD1 with POU-loaded RIDD2 in the vagina. The method includes delivering, with RIDD2, a therapeutically effective amount of the lactic acid to the vagina and maintaining vaginal pH at or below 4.5.

In an embodiment, the method includes repeating the POU-loading of RIDD1 and POU-loading RIDD2, repeating the alternating replacement of POU-loaded RIDD1 with POU-loaded RIDD2 (and repeating the replacement of RIDD2 with a POU-reloaded RIDD1) in the vagina, to continuously maintain vaginal pH at or below 4.5 or less for a time duration from a day, or a week, or a month, or 2 months, or 3 months, or 4 months, or 5 months, or 6 months, or 9 months to 12 months, or 24 months, or 36 months (or any time duration therebetween) or more.

An advantage of the present disclosure is the provision of a genital tract treatment system that is reusable.

An advantage of the present disclosure is the provision of a genital tract treatment system that is economical.

An advantage of the present disclosure is the provision of reusable genital tract treatment system that promotes the environment because it is used multiple times before being discarded.

An advantage of the present disclosure is the provision of a reusable genital tract treatment system that is easy to use.

An advantage of the present disclosure is the provision of a reusable genital tract treatment system that enables continuous delivery of a therapeutic agent to the genital tract for very long time durations.

An advantage of the present disclosure is the provision of a reusable genital tract treatment system that provides point-of-use load and point-of-use reload of the delivery device by the end user.

An advantage of the present disclosure is the provision of a reusable genital tract treatment system that avoids manufacturer-loaded delivery devices and avoids factory-loaded delivery devices.

An advantage of the present disclosure is a system and method for repeated point-of-use reloading of two reusable intravaginal delivery devices that are alternatingly cycled into and out of the vagina to provide continuous therapeutic treatment to the vagina for exceptionally long time durations.

An advantage of the present disclosure is the provision of reusable intravaginal delivery devices with a long lifespan.

An advantage of the present disclosure is a genital tract treatment system that provides treatment for extremely long time durations because the treatment system entails a point-of-use load and reload protocol which is easy to perform repeatedly by the end user.

An advantage of the present disclosure is a genital tract treatment system that is viable and economically accessible to persons living in low resource countries (such as developing countries, sometimes referred to as third world countries) because the system is reusable, point-of-use loadable and reloadable, economical, easy to use for the end user, and provides continuous extended term (1 day to 1 year, 2 years, (and any time duration therebetween), or more) delivery of a therapeutic agent to the genital tract.

BRIEF DESCRIPTION OF THE DRAWINGS

FIG. 6 is a graph showing the release of lactic acid over time from a polyurethane RIDD in accordance with an embodiment of the present disclosure.

FIG. 7 is a graph showing the release of lactic acid over time from a polyurethane RIDD in accordance with an embodiment of the present disclosure.

DETAILED DESCRIPTION

1. Point-of-Use Load Intravaginal Delivery Device

Figure 1:
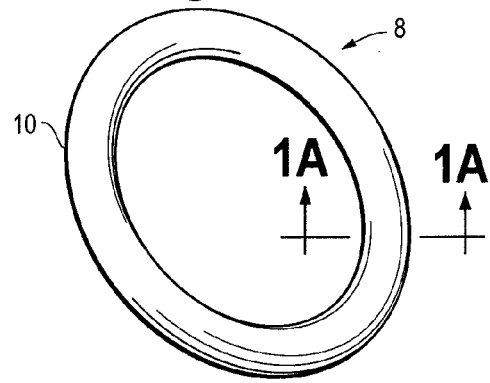
FIG. 1 is a perspective view of a reusable intravaginal delivery device in accordance with an embodiment of the present disclosure.

The present disclosure provides a system. In an embodiment, a point-of-use load intravaginal delivery system is provided and includes a first reusable intravaginal delivery device (RIDD1) and a second reusable intravaginal delivery device (RIDD2) (collectively "RIDD"). Each RIDD has a permeable wall. The permeable wall defines an enclosed interior reservoir. The reservoir is adapted to receive a therapeutic agent. The system further includes a point-of-use recharge kit. The point-of-use recharge kit includes a therapeutic agent. The point-of-use recharge kit provides or otherwise enables end user loading for at least one (or both) of the RIDDs with the therapeutic agent.

The term "point-of-use" (or "POU"), as used herein, is the location (i.e., the "point") of the end user of the system. In other words, the point-of-use is the location of the end user (a person—male or female) to which the RIDD is administered. The term "end user" is the person into which the RIDD is to be inserted. The term "POU-loading" is the loading and reloading of at least one RIDD with therapeutic agent by the end user (or an agent of the end user). The term "POU-reloading" is the loading or charging of a RIDD with a therapeutic agent after the RIDD has delivered therapeutic agent to the genital tract. The terms "reload" and "recharge" may be used interchangeably. The term "agent" is a person (a family member of the end user, a friend of the end user, or a health care provider for the end user, for example) located with the end user and excludes the RIDD manufacturer, the RIDD seller/distributor, the RIDD regulatory agency, and any combination thereof.

POU is distinct from point-of-manufacture or point-of-purchase. Conventional IDDs are produced and prepared for use at the point of manufacture (or somewhere along the production chain), or at the point of purchase, as in compounding pharmacies. A conventional point-of-manufacture IDD, or a point-of-purchase IDD is ready for use when received by the end user. Conventional IDDs are single use devices and are not designed to be re-used. In other words, a conventional IDD is ready for use when it leaves the factory, or when it leaves the point of purchase and is discarded after one use.

In contrast, the present system is a POU system whereby the end user (or an agent of the end user) loads and reloads, or self-loads, the RIDD with the therapeutic agent and subsequently self-administers or otherwise inserts the POU-loaded RIDD into her own genital tract. In this way, the end user loads and reloads the RIDD with therapeutic agent.

The present POU system provides the end user with the elements for load/reload of the RIDD with therapeutic agent. The present POU system advantageously (1) promotes and enables multi-use of the RIDDs, (2) promotes and enables extended and consistent wear of the RIDDS by the end user, (3) promotes and enables continuous delivery of therapeutic agent to the genital tract for days, weeks, months, a year, even greater than a year, (4) promotes and enables easy and continuous exchange by the end user of an expended RIDD with a POU-reloaded RIDD, and (5) promotes quality control by way of end user inspection and maintenance of the RIDDs during the reload and re-insertion cycle.

a. Reusable Intravaginal Delivery Device

The present point-of-use load intravaginal delivery system includes a first reusable intravaginal delivery device and a second reusable intravaginal delivery device. The term "reusable intravaginal delivery device" (or "RIDD") is a multi-use intravaginal delivery device insertable (and re-insertable) and removable (and re-removable) into/from the genital tract (e.g., the vagina), the RIDD providing a therapeutically effective amount of a therapeutic agent into the genital tract (vagina). Friction fit between the RIDD and the vaginal wall, for example, holds the RIDD within the vagina. Alternatively, the size discrepancy between the uncompressed ring and the vaginal introitus can hold the RIDD within the vagina. Non-limiting examples of suitable RIDD configurations include toroid-shaped devices, partial toroid-shaped devices, annular devices, ovoid devices, cylindrical devices, rectilinear devices, and substantially rectilinear, devices. When ring shaped, the cross sectional profile of the RIDD may be round or ovoid. The term "multi-use" indicates that the present RIDD is compositionally and physically resilient and has the structural integrity to be inserted, worn, removed, loaded/reloaded at least two times, or two or more times. It is understood that the description herein of the RIDD applies equally to RIDD1 and RIDD2.

In an embodiment, the present system includes three, four, or more RIDDs.

In an embodiment, the life span of the RIDD is from 2 to 200 cycles, wherein a "cycle" is defined as the following events: genital tract insertion of loaded RIDD, delivery of therapeutically effective amount of therapeutic agent from the RIDD to the genital tract, removal of RIDD from the genital tract, and reload of therapeutic agent into the RIDD.

In an embodiment, the RIDD is a reusable intravaginal ring 8 as shown in FIG. 1. A "reusable intravaginal ring" or "RIVR" is a RIDD that is a toroid-shaped device and includes complete toroid-shaped devices, partial toroid-shaped devices, ovoid-shaped devices, and ring-shaped devices. The outer diameter of the RIVR 8 is from 35 mm, or 40 mm, or 50 mm, or 60 mm to 70 mm, or 80 mm, or 90 mm, or 100 mm. The cross-sectional diameter of the RIVR 8 is from 1 mm, or 2 mm, or 3 mm, or 4 mm to 8 mm, or 10 mm to 12 mm, or 14 mm, or 16 mm, or 18 mm, or 20 mm. The RIVR 8 cross sectional profile may be a circle as in FIG. 1A or ovoid as in FIG. 1B.

Figure 1A:
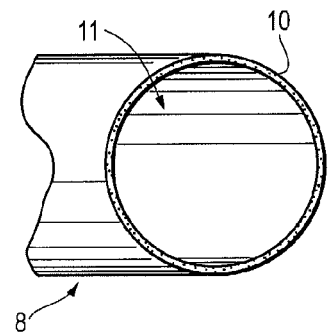
FIG. 1A is a sectional view of the device of FIG. 1 taken along line 1A-1A of FIG. 1.
Figure 1B:
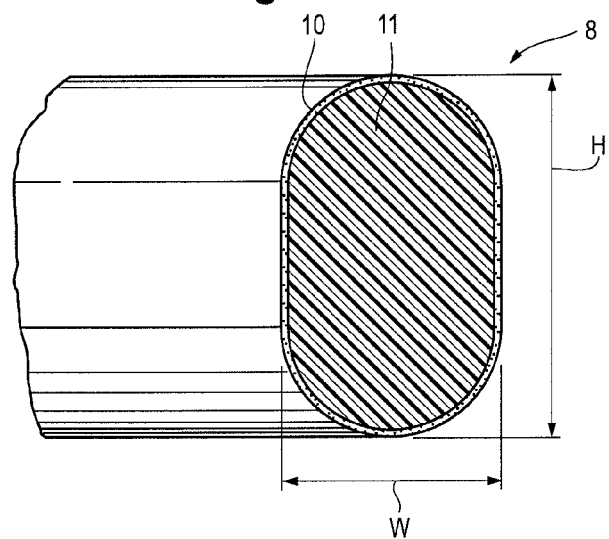
FIG. 1B is a sectional view of a reusable intravaginal delivery device where the sectional profile is ovoid in accordance with an embodiment of the present disclosure.

In an embodiment, the RIVR 8 has an ovoid cross-sectional shape with an aspect ratio (ratio of height to width) from 2:1 to 1.2:1 as shown in FIG. 1B. The height of the RIVR 8, shown as "H" in FIG. 1B is from 3 mm, or 5 mm to 8 mm, or 10 mm. The width of the RIVR 8, shown as "W" in FIG. 1B, is from 2 mm to 6 mm. The height and width dimensions of RIVR 8 may increase by 10% to 30% upon swelling when the RIVR 8 is loaded with the therapeutic agent and water or other solvent. In a further embodiment, RIVR 8 has an ovoid cross-sectional shape and has a height of 6.2 mm and a width of 3.7 mm.

b. Permeable Wall

In an embodiment a permeable wall forms the RIDD. The permeable wall has a thickness from 0.02 mm, or 0.05 mm, or 0.1 mm to 0.5 mm, or 1.0 mm, or 1.5 mm, or 2.0 mm. The permeable wall is solid and excludes macroporous structures such as foams and sponges. The permeable wall is composed of a permeable biocompatible polymeric material and forms an enclosed interior reservoir.

A "biocompatible polymeric material" is a material that does not impart a toxic or an injurious effect on a biological system. Nonlimiting examples of suitable biocompatible polymeric materials for the permeable wall include polysiloxane (silicone), ethylene/vinyl acetate copolymer (EVA), polyethylene, polypropylene, ethylene/propylene copolymer, acrylic acid polymer, ethylene/ethyl acrylate copolymer, polytetrafluoroethylene (PTFE), polyurethane, polybutadiene, polyisoprene, poly(methacrylate), polymethyl methacrylate, styrenebutadiene-styrene block copolymers, poly(hydroxyethylmethacrylate) (pHEMA), polyvinyl chloride, polyvinyl acetate, polyether, polyacrylonitrile, polyethylene glycol, polymethylpentene, polybutadiene, polyhydroxy alkanoate, poly(lactic acid), poly(glycolic acid), polyanhydride, polyorthoester, hydrophilic polymers such as the hydrophilic hydrogel, cross-linked polyvinyl alcohol, neoprene rubber, butyl rubber, and combinations thereof.

In an embodiment, the permeable wall is composed of a polyurethane or a silicone.

In an embodiment, the permeable wall is composed of polyurethane. The polyurethane may be a polyether polyurethane, a polyester polyurethane, and combinations thereof. Polyether polyurethanes, in particular, are well-suited for multi-use because polyether polyurethane is resistant to hydrolysis. Aromatic and aliphatic polyurethanes may also be used. Aromatic polyurethanes are known to soften less with exposure to moisture. In addition, the hydrophilicity of polyurethane can be varied in order to achieve different loading rates and release rates. More hydrophilic polyurethane (such as Tecophilic® HP-60D-20, Lubrizol, Inc.) and less hydrophilic polyurethane (such as Tecoflex® EG-85A, Lubrizol, Inc.) may be selected to achieve a desired therapeutic agent release rate.

In an embodiment, the permeable wall is composed of silicone.

c. Reservoir

The permeable wall forms a reservoir. The reservoir is adapted to receive, or otherwise hold, a therapeutic agent. The reservoir can be an enclosed interior space formed by the permeable wall. Alternatively, the reservoir can be a material such as a liquid, a solid material, or a semi-solid material. The reservoir can hold the therapeutic agent in an amount from 0.1 ml, or 0.2 ml, or 0.3 ml, or 0.5 ml, or 1 ml to 5 ml, or 8 ml, or 10 ml, or 15 ml, or 20 ml.

A reservoir material is located in the reservoir for releasably containing the therapeutic agent. In an embodiment, the reservoir material is a liquid, a semi-solid, a solid, and any combination thereof.

In an embodiment, the reservoir may be hollow and continuous, or hollow and partitioned.

In an embodiment, the reservoir contains a liquid. The liquid may be a low viscosity liquid such as water or another solvent. The therapeutic agent is soluble in the reservoir liquid.

In an embodiment, the reservoir contains a semi-solid. Suitable semi-solid materials include gels, hydrogels, sponge material, or foam material with gas-filled interstices, and any combination thereof.

In an embodiment, the reservoir material is selected so that the therapeutic agent to be released by the RIDD is sufficiently soluble in the reservoir material to hold the desired quantity of therapeutic agent.

In an embodiment, the reservoir material is a solid material. The reservoir solid material may be the same as, or different than, the material of the permeable wall. Nonlimiting examples of suitable solid material for the reservoir include polysiloxane (silicone), poly(ethylene-co-vinyl acetate), styrene-butadiene-styrene block copolymer, poly(hydroxyethylmethacrylate) (pHEMA), polyvinyl chloride, polyvinyl acetate, poly(vinyl alcohol), polyester, poly(acrylic acid), polyether, polyurethane, polyacrylonitrile, polyethylene glycols, polyethylene, polypropylene, polymethylpentene, polybutadiene, cellulose and its derivatives, polyamide, and mixtures thereof.

In an embodiment, each material for the permeable wall and for the reservoir is selected to obtain a desired therapeutic agent release profile. The permeable wall is selected to have a lower permeability (with respect to the therapeutic agent) than the permeability of the reservoir material. The permeable wall thereby controls the release of therapeutic agent from the reservoir material, through the permeable wall to the genital tract, thus reducing or eliminating burst effects (i.e., extremely rapid initial release rates), and extending the release duration. In this way, the permeable wall is a "metering layer" and delivers the therapeutic agent to the vaginal cavity in a continuous, sustained-release, and uniform manner.

A "metering layer," as used herein, is a permeable wall that slows diffusion of the therapeutic agent to a rate slower than the diffusion rate of the therapeutic agent from the reservoir material alone.

When the reservoir is a solid material, the permeable wall may be formed by way of coextrusion, dip-coating, spray-coating, injection molding, two-shot molding, with, or on, the outer surface of the reservoir material. The permeable wall may be uniform, continuous, discontinuous, or perforated. The permeable wall may or may not cover the entire outer surface of the reservoir material.

In an embodiment, the permeable wall is coextensive, or substantially coextensive, with the outer surface of the solid reservoir material.

Nonlimiting examples of suitable material configurations for the permeable wall and the reservoir material are provided in Table A below.

TABLE A

| Permeable wall | Reservoir |
|---|---|
| 20% ws PU (Tecophilic HP-60D-20) | 60% ws PU (Tecophilic HP-60D-60 |
| 20% ws PU (Tecophilic HP-60D-20) | 100% ws PU Tecophilic HP-93A-100) |
| PU -Tecoflex EG-85A | 20% ws PU (Tecophilic HP-60D-20 |
| PU--Tecoflex EG-85A | 60% ws PU (Tecophilic HP-60D-60 |
| PU--Tecoflex EG-85A | 100% ws PU (Tecophilic HP-93A-100) |
| Silicone-Nusil MED-6605 | 60% ws PU Tecophilic HP-60D-60 |

In an embodiment, the RIDD is a RIVR 8 as shown in FIGS. 1A, and 1B. The RIVR 8 has a permeable wall 10 that forms a reservoir 11, and the permeable wall has a permeability lower than the permeability of the reservoir material. In an embodiment, the reservoir 11 has a volume from 0.2 ml to 20 ml.

In an embodiment, the permeable wall 10 has a thickness from 0.01 mm to 2.0 mm.

FIG. 1B shows RIVR 8 with a cross-sectional shape that is ovoid.

Figure 1C:
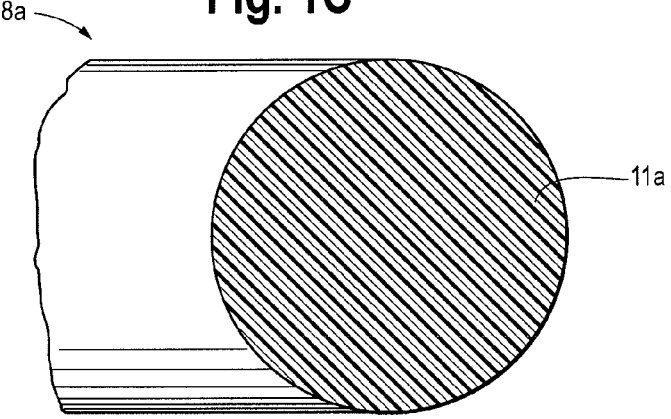
FIG. 1C is a sectional view of a reusable intravaginal delivery device in accordance with an embodiment of the present disclosure.

In an embodiment, RIVR 8a is composed of a solid reservoir material 11a as shown in FIG. 1C. The therapeutic agent moves into and out of the reservoir material through the outer surface of the reservoir material 11a. In a further embodiment, the reservoir material 11a is a monolithic polyurethane, and the outer surface of this monolithic structure constitutes the permeable surface.

d. Therapeutic Agent

The reservoir is adapted to receive a therapeutic agent. A "therapeutic agent," as used herein, is an agent that produces a desired physiological effect. The therapeutic agent treats or prevents bacterial infection, fungal infections, STIs, and any combination thereof in the genital tract. Nonlimiting examples of suitable therapeutic agents include lactic acid, antimicrobial agent, antiviral agent, antibacterial agent, essential oils, such as tea tree oil, cations or elements, such as Cu, or Ag, polyene antimycotic, imidazole, triazole, allyamines, echinocandin, aciclovir, amantadine, artemisinin derivatives, alcohols, quartenary ammmonium compounds, boric acid, chlorhexidine gluconate, hydrogen peroxide, urea hydrogen peroxide, iodine, mercurochrome, octenine dihydrochloride, phenolic (carbolic acid) compounds, sodium chloride, sodium hypochlorite, and combinations thereof. Additional classes of therapeutic agents include anticancer agents, urinary antispasmodics, and proteins or nucleic acids intended as vaccines.

Nonlimiting examples of suitable antimicrobial agents include metronidazole, clindamycin, ampicillin, amoxicillin, tetracycline, and doxycycline. Nonlimiting examples of suitable antiviral agents include anti herpes agents, and antiretrovirals (including nucleoside or non-nucleoside reverse transcriptase inhibitors), protease inhibitors, integrase inhibitors, fusion inhibitors, chemokine receptor antagonists, and specifically including without limitation acyclovir, famciclovir, ganciclovir, valacyclovir, tenofovir, tenofovir disoproxil fumarate, dapivirine, saquinavir and maraviroc. Nonlimiting examples of suitable antifungal agents include azole derivatives such as itraconazole, miconazole, terconazole, isoconazole, fenticonazole, fluconazole, ketoconazole, butoconazole and econazole, clotrimazole, and 5-fluorocytosine.

Nonlimiting examples of suitable antibacterial agents include metronidazole, clindamycin, tetracycline, amoxicillin, ampicillin, erythromycin, doxycycline, lumefloxacin, norfloxacin, afloxam, ciproflaxin, azitromycin, cefltoxine, and chlorquinaldol.

In an embodiment, the therapeutic agent is lactic acid. The lactic acid may be in any suitable phase such as liquid, solid, semi-solid, or aqueous solution. When delivered to the epithelial surface of the genital tract, the lactic acid produces the desired physiological effect of (1) maintaining vaginal pH at 4.5 or less, (2) providing an anti-microbial concentration of lactic acid to the genital tract (vagina), (3) preventing pathogenic infection, reducing pathogenic infection, or any combination thereof. The lactic acid can be L-lactic acid (L-lactic acid free, or substantially free, of D-lactic acid), D-lactic acid, and a combination of L-lactic acid and D-lactic acid.

In an embodiment, the therapeutic agent is a lactic acid composition. The lactic acid composition is an aqueous solution of lactic acid and contains from 10 wt % to 90 wt % lactic acid and from 90 wt % to 10 wt % water. The lactic acid composition has a pH of 1.0, or 1.5, or 1.7, to 2.0, or 2.5, or 3.0, or 3.5, or 4.0, or 4.5. A nonlimiting example of suitable lactic acid composition is PURAC® PF 90 (90 wt % L-lactic acid, Purac Bioquimica SA), or Lactic Acid, Racemic, 85% syrup USP, (Spectrum Chemicals), undiluted, or at various dilutions, and at various degrees of partial neutralization.

The therapeutic agent may contain one or more additives. Nonlimiting examples of suitable additives include solvent, pharmaceutical agent, pharmaceutical excipient, buffering agent (molecular weight and/or pH), preservative, anti-oxidant, delivery agent, viscosity-adjusting agent, and any combination thereof. Nonlimiting examples of solvents include water, mineral oils, vegetable oils, alcohols. Nonlimiting examples of suitable tonicity and/or ionic strength modifiers include sodium chloride, potassium chloride, glycerin, propylene glycol, and polyethylene glycol. Nonlimiting examples of suitable low molecular weight buffering agents include monobasic potassium or sodium phosphate, dibasic potassium or sodium phosphate. Nonlimiting examples of suitable high molecular weight buffers include polycarbophil, carboxylated polysaccharides such as alginic acid or carboxymethylcellulose. Nonlimiting examples of suitable preservatives include methylparaben, propylparaben, benzoic acid, sorbic acid, disodium or other forms of ethylenediaminetetraacetic acid (EDTA).

In an embodiment, the reservoir material and the concentration of therapeutic agent during POU-load/POU-reload are chosen so that the reservoir material can be saturated or otherwise sufficiently loaded within the POU-reload interval.

In an embodiment, the POU-reload interval is the same, or substantially the same, as the wear interval for the POU-loaded/reloaded RIDD. This results in an invariant initial concentration of therapeutic agent immediately after the recharging step and contributes to a predictable release rate during wear.

In an embodiment, each RIDD is a diffusion-loaded RIDD. A "diffusion-loaded RIDD," (or "diffusion-reloaded RIDD") as used herein, is a RIDD that loads and reloads therapeutic agent solution (aqueous solution or non-aqueous solution) by way of passive diffusion. The term "passive diffusion," as used herein, is the transport, by way of random thermal motion and without an input of energy, of the therapeutic agent across the permeable wall (or across the reservoir outer surface) and into the reservoir. Passive diffusion excludes convection, advection, and capillary action.

2. Point-of-Use Recharge Kit

The present POU load vaginal delivery system includes a point-of-use recharge kit. The point-of-use recharge kit includes at least two RIDDs, the therapeutic agent and optionally a recharge vessel and cleaning equipment. A "point-of-use recharge kit" or "POU recharge kit," as used herein, is a kit for loading/reloading the RIDD(s) with therapeutic agent by the end user. In other words, the POU recharge kit is configured to be used by the end user for load/reload of the RIDDs. The POU recharge kit advantageously avoids the necessity of RIDD load/reload by the manufacturer, by a governmental agency, by a compounding pharmacy, by a health care provider, or any combination of the foregoing.

In an embodiment, the POU recharge kit is located with the end user (as opposed to being located at the manufacturer, at the seller/distributor, at a health care facility, at a pharmacy, or a clinic). The POU recharge kit may be located at the end user's home, the end user's workplace, or otherwise travels with, or accompanies, the end user. In a further embodiment, the POU recharge kit is portable/transportable and accompanies the end user.

In an embodiment, the POU recharge kit includes one or more of the following components in addition to the therapeutic agent: cleaning solution, a cleaning device, a recharge vessel, and any combination thereof. Nonlimiting examples of suitable cleaning devices include a brush, a cloth, a swab, a cotton ball, and any combination thereof. In a further embodiment, the POU recharge kit includes a container of a bulk amount of therapeutic agent. A "bulk amount of therapeutic agent," as used herein, is an amount of therapeutic agent that is greater than the volume of the RIDD reservoir. The bulk amount of therapeutic agent can be solid or liquid.

In an embodiment, one RIDD (RIDD1) is located in a genital tract (e.g., a vagina) and the other RIDD (RIDD2) is in operative communication with at least one of the following POU recharge kit components: the therapeutic agent, the recharge vessel, the cleaning solution, the cleaning device, and combinations thereof. The RIDD is in "operative communication" with the therapeutic agent when the RIDD is in fluid communication with the therapeutic agent. Fluid communication includes immersion (wholly or partially) of the RIDD in liquid or aqueous therapeutic agent; release, and/or diffusion (into or out of the RIDD) of the therapeutic agent to/from the RIDD. The RIDD may also be in operative communication with the therapeutic agent when the therapeutic agent is provided in the form of a powder coating the surface of the RIDD.

The RIDD operatively communicates with the recharge vessel when the RIDD is placed within the recharge vessel (and is optionally in contact with, or immersed in, liquid or aqueous therapeutic agent present in the recharge vessel). The RIDD operatively communicates with the cleaning solution when the RIDD is being cleaned with the cleaning solution. The RIDD operatively communicates with the cleaning device when the RIDD is being cleaned with the cleaning device. In this way, as one RIDD is treating the genital tract, the other RIDD is being prepared to treat the genital tract. When RIDD1 (the RIDD in the genital tract) is expended, RIDD2 is ready to replace RIDD1 in the genital tract. The use of one RIDD and simultaneous POU recharge of the other RIDD provides a continuous genital tract treatment protocol with an extended time duration that is self-administered by the end user.

The POU recharge kit enables the end user to load/reload at least one of the RIDDs with the therapeutic agent. The term "POU recharge" includes the following events: (1) the end user removes an expended RIDD from the genital tract (e.g., the vagina), (2) (event 2 is an optional event) the end user cleans/rinses the expended RIDD with the cleaning solution, the cleaning device, water, and any combination thereof, (3) the end user places the expended RIDD in operative communication with the therapeutic agent for a time duration sufficient for the expended RIDD to load (or diffusion-load) with the therapeutic agent or fill or otherwise load the RIDD reservoir with therapeutic agent and produce a recharged RIDD, and (4) the end user re-administers the recharged RIDD to the genital tract (i.e., the vagina).

Figure 2:
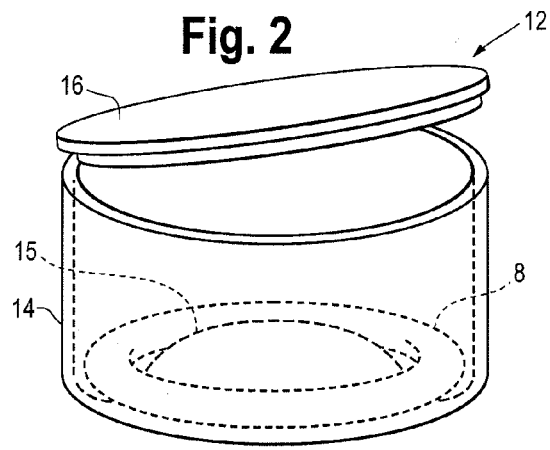
FIG. 2 is a perspective view of a recharge vessel in accordance with an embodiment of the present disclosure.
Figure 3:
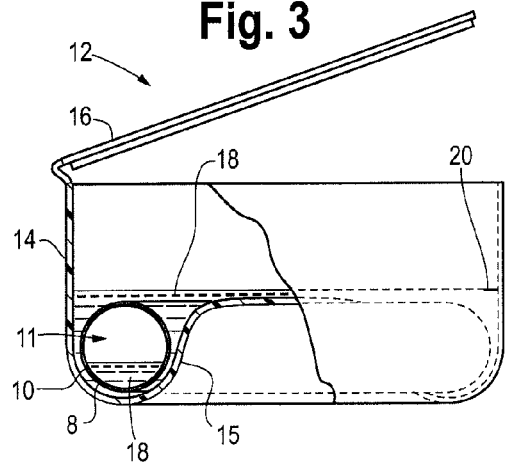
FIG. 3 is a breakaway elevational view of a recharge vessel in accordance with an embodiment of the present disclosure.
Figure 14:
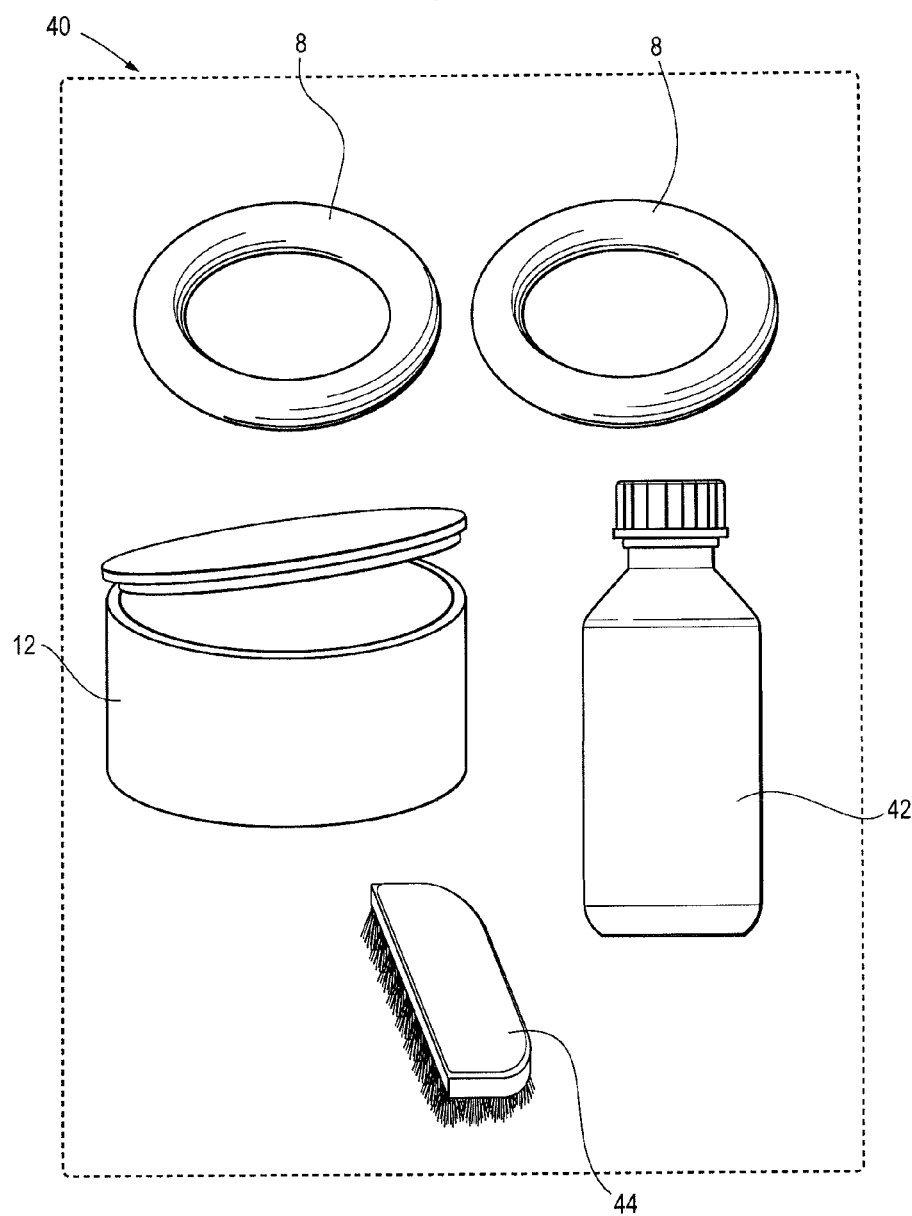
FIG. 14 is a perspective view a point-of use recharge kit in accordance with an embodiment of the present disclosure.

In an embodiment, a POU recharge kit 40 includes a first RIVR 8 a second RIVR 8, a recharge vessel 12, a container of a bulk amount of therapeutic agent 42, and an optional cleaning brush 44 as shown in FIGS. 2, 3, and 14. The recharge vessel 12 is adapted to receive a RIDD and RIVR 8 in particular. In an embodiment, the RIDD is RIVR 8 as shown in FIGS. 2-3. The recharge vessel 12 includes a container 14 and a lid 16. When closed, the lid 16 may form a watertight seal on the container 14. The end user removes an expended RIVR 8 from the vagina and optionally cleans the expended RIVR 8 with cleaning solution, the cleaning device, water, and any combination thereof A biofilm may form on the RIVR 8 while in the vagina. Removing the biofilm with the cleaning solution and/or cleaning brush 44 (FIG. 14) can promote effective recharge of the RIVR 8. The end user places the expended RIVR 8 in the recharge vessel 12. The end user adds liquid (or aqueous solution) containing therapeutic agent 18 to the container 14 and immerses (partially or whole immersion) the RIVR 8 in the liquid therapeutic agent 18. It is understood that the liquid therapeutic agent 18 may be an aqueous solution or a nonaqueous solution. The end user closes the lid 16 on the container 14 and (optionally) forms a watertight seal. The RIVR 8 subsequently becomes loaded with the therapeutic agent 18 by way of diffusion through the permeable wall 10.

In an embodiment, the POU recharge kit 40 includes instructions for use. The instructions provide the end user with immersion time durations for full or complete loading of the RIDD with therapeutic agent. Diffusion-load kinetics during recharge will be dictated by the RIDD structure/composition (partition coefficient, permeability) as well as the diffusion properties for the therapeutic agent (molecular weight, solubility, viscosity, pH, etc).

In a further embodiment, the recharge vessel 12 has an inner volume from 1×, or 1.5×, or 2×, or 3× to 4×, or 5×, or 6×, the volume of the RIDD reservoir. In this way, the amount of therapeutic agent used for POU recharge is economized during POU recharge. The bottom of the container 14 may include a raised dome 15. Raised dome 15 forms the bottom surface of the container 14 so as to reciprocally match the ring shape of RIVR 8. A fill-line 20 (FIG. 3) may be scored on the inner surface of the container 14 indicating the proper amount of liquid therapeutic agent 18 to be added for full load/reload. In this way, the end user is enabled to add a sufficient and economical amount of the liquid therapeutic agent 18 to the recharge vessel 12—advantageously eliminating/reducing waste of the liquid therapeutic agent 18. The recharge vessel 12 promotes ease-of-use of the POU-recharge kit by the end user.

In an embodiment, the recharge vessel 12 includes a raised dome 15 that promotes efficient and economical addition of the therapeutic agent 18 by economizing the therapeutic agent contact volume with the RIVR 8. The raised dome 15 thereby reduces/eliminates waste of the therapeutic agent 18. The RIVR 8 is placed in the recharge vessel 12 and the liquid therapeutic agent 18 is added to the fill line 20. During this dwell period, the RIVR 8 becomes loaded with the therapeutic agent 18 by way of diffusion through the permeable wall 10.

In an embodiment, the wear duration of the POU-loaded or POU-reloaded RIVR 8 in the vagina is the same as the diffusion-load/reload duration or the diffusion-reload duration of the RIVR 8 in the recharge vessel 12. In a further embodiment, the wear duration (and the load/reload duration) for RIVR 8 is from 4 days, or 6 days to 7 days, or 8 days.

a. RIVR is Releasably Openable

Figure 4:
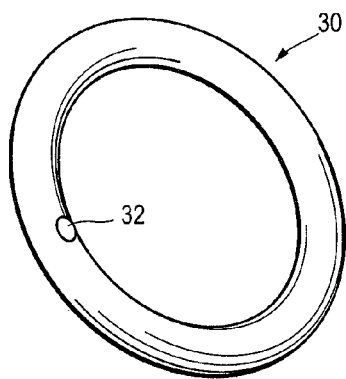
FIG. 4 is a perspective view of a reusable intravaginal ring (RIVR) in accordance with an embodiment of the present disclosure.
Figure 5:
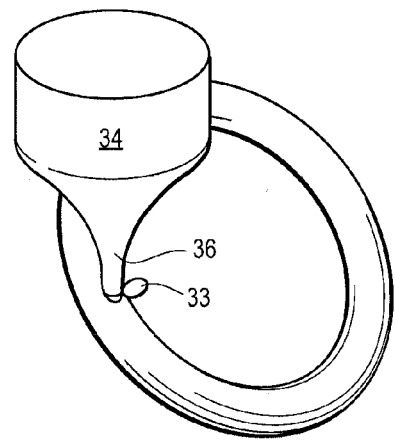
FIG. 5 is a perspective view of a RIVR in operative communication with a container of a bulk therapeutic agent in accordance with an embodiment of the present disclosure.

In an embodiment, one or both RIDDs is a RIVR 30 as shown in FIGS. 4 and 5. The RIVR 30 includes an inlet 32 located on the inner annular surface of the RIVR 30. The inlet 32 is releasably openable by way of closure 33. The closure 33 is openable and closable, the closure 33 releasably closing inlet 32 to form a watertight seal. The inlet 32 is closed to form a watertight seal with the RIVR 30 before the RIVR 30 is inserted into in the vagina. The POU recharge kit 40a includes a container of a bulk amount of therapeutic agent 34, the container 34 having a port 36 for reciprocal engagement with the inlet 32. The end user places the port 36 into reciprocal engagement with the inlet 32 to load/reload the RIVR 30 with the therapeutic agent. Addition of the therapeutic agent into the inlet 32 loads/reloads the RIVR 30. In this way, the POU recharge time is reduced because diffusion is avoided. In a further embodiment, the therapeutic agent is a lactic acid solution, the lactic acid solution being end user loaded/reloaded into the inlet 32.

The closure 33 may include structure to prevent flow of therapeutic agent from the reservoir through the closure 33 and into the vagina. In this way, closure 33 prevents harm to the vagina by preventing a burst of therapeutic agent through the closure 33.

The present POU loaded intravaginal delivery system provides a new dimension to genital tract treatment, therapy and care with here-to-fore unforeseeable and unpredictable advantages. The present POU system provides continuous use and re-use of recharged RIDDs directly by the end user. This continuous RIDD recharge feature of the present POU system delivers long-term, continuous genital tract treatment precisely to the infected area—the end user's genital tract. The alternating and continuous RIDD recharge and replace (in the vagina) feature of the present POU system enables the end user with easy, convenient, and long-term provision of therapeutically effective RIDDs. The present POU system greatly improves treatment efficacy and substantially reduces the chance of recurrence for genital tract infection—especially for highly recurrent ailments such as BV. The present POU system provides and enables the end user with easy-to-use treatment components for delivering reliable, consistent, steady, and large amounts of therapeutic agent to the genital tract over exceptionally long continuous time durations such as greater than one week, or greater than two weeks, or months to years.

3. POU System Operation

Each RIDD is configured to release and load with the therapeutic agent by way of diffusion into and out of the permeable wall. Each RIDD is further configured to deliver a therapeutically effective amount of the therapeutic agent to the genital tract. Loading is by diffusion of the therapeutic agent rather than by way of convection, advection, capillary flow, or other means of bulk fluid flow as with sponges or fibrous devices such as tampons. Alternatively loading of the RIVR 30 may be performed by bulk loading through the inlet 32. These provisions avoid the disadvantages of the macroporous surfaces of sponges and tampons, which may encourage the growth of harmful microorganisms, and make cleaning difficult.

In an embodiment, the release rate of the therapeutic agent from the RIDD is the same, or substantially the same, as the diffusion-loading rate of the therapeutic agent into the RIDD.

In an embodiment, the therapeutic agent is a lactic acid composition. Each RIDD has an intravaginal lactic acid release rate of 1 mg/day, or 10 mg/day, or 50 mg/day, or 200 mg/day to 500 mg/day, or 1,000 mg/day, or 10,000 mg/day for 1 day, or 2 days, or 3 days, or 4 days, or 5 days, or 6 days to 7 days, or 15 days, or 30 days.

In an embodiment, the therapeutic agent is a lactic acid composition. Each RIDD has a lactic acid composition diffusion-load rate of 1 mg/day, or 10 mg/day, or 50 mg/day, or 200 mg/day to 500 mg/day, or 1,000 mg/day, or 10,000 mg/day for 1 day, or 2 days, or 3 days, or 4 days, or 5 days, or 6 days to 7 days, or 15 days, or 30 days.

In an embodiment, the present POU system includes the configuration whereby RIDD1 is in the vagina. RIDD2 is in operative communication with a component of the point-of-use recharge kit. In other words, the present system includes the configuration whereby RIDD1 is in the vagina and RIDD2 simultaneously is in operative communication with at least one component of the POU recharge kit. In a further embodiment, lactic acid composition is in the reservoir of RIDD1 and RIDD1 is located in a vagina.

In an embodiment, the present POU system includes the configuration whereby RIDD1 is in the vagina. RIDD2 is in the recharge vessel with an amount of the therapeutic agent, namely the lactic acid composition. In this configuration, RIDD1 is delivering a therapeutically effective amount of the lactic acid composition to the vagina while RIDD2 is in the recharge vessel and is simultaneously loading/reloading with the lactic acid composition. Thus, once RIDD1 is expended, RIDD1 is removed from the vagina and replaced with load/reloaded RIDD2.

4. Device

The present disclosure provides a device. In an embodiment, a device is provided and includes a POU-loaded RIDD1, a POU-loaded RIDD2, therapeutic agent and optional recharge vessel and cleaning equipment. POU-loaded RIDD1 is loaded/reloaded with a therapeutic agent. The device also includes a point-of-use loaded RIDD2. RIDD2 is POU-loaded with the therapeutic agent. In a further embodiment, the therapeutic agent is a lactic acid composition. POU-loaded RIDD1 and POU-loaded RIDD2 are alternately (non-simultaneously) inserted into a vagina in a continuous and alternating manner, each device delivering a therapeutically effective amount of the therapeutic agent to the vagina. The POU-loaded RIDD2 replaces the POU-loaded RIDD1 in the vagina when the POU-loaded RIDD1 is expended, or otherwise depletes its reservoir of therapeutic agent. POU-loaded RIDD1 replaces the POU-loaded RIDD2 in the vagina when the POU-loaded RIDD2 is partially or fully expended, or otherwise exhausts its reservoir of therapeutic agent. The alternating replacement of POU-loaded RIDD1 with POU-loaded RIDD2 (and vice versa) provides continuous delivery of the therapeutic agent to the genital tract or vagina for extremely long durations—anywhere from 1 day, or 1 week, or 1 month, or 2 months, or 3 months, or 4 months, or 5 months, or 6 months, or 9 months to 12 months, or 18 months, or 24 months, or 36 months (and any time duration therebetween) or longer.

5. Method

The present disclosure provides a method. In an embodiment, a method for delivering a therapeutic agent to a vagina is provided. The method includes providing the POU recharge kit to the end user as disclosed above. The POU recharge kit includes RIDD1, RIDD2, and the therapeutic agent. Each RIDD has a permeable wall defining an enclosed interior reservoir. Each RIDD is adapted to receive a therapeutic agent. The POU recharge kit optionally includes the recharge vessel and cleaning equipment. The method further includes enabling, with the kit, point-of-use loading and reloading of the therapeutic agent to at least one RIDD.

As used herein, the term "enabling" or "enable" and like terms, is to give the ability to, to empower, or otherwise to effectuate, end user loading/reloading of the RIDD(s). Thus, providing the present point-of-use recharge kit with at least two RIDDs, a container of the therapeutic agent, optional recharge vessel, and optional cleaning equipment to the end user (optionally along with instructions on how to use the kit) enables the point-of-use load/reload of the RIDD(s) by the end user. In a further embodiment, the method includes point-of-use loading/reloading one, or both, of the RIDDs, by the end user.

In an embodiment, the method includes inserting RIDD1 into the vagina and delivering a therapeutically effective amount of the therapeutic agent to a vagina with RIDD1.

In an embodiment, the method includes point-of-use loading RIDD2 with the therapeutic agent, removing the RIDD1 from the vagina, inserting the RIDD2 into the vagina; and further delivering, with RIDD2, a therapeutically effective amount of the therapeutic agent into the vagina. In a further embodiment, RIDD2 is POU-loaded/-reloaded when RIDD1 is in the vagina.

In an embodiment the method includes the use of more than two RIDDs, with multiple RIDDs being POU-loaded/-reloaded while another RIDD is in contact with the vagina. In this way, the duration of loading and the amount loaded can be extended beyond the time a worn RIDD is in place in the vagina.

The disclosure provides another method. In an embodiment, a method for delivering a therapeutic agent to a vagina is provided. The method includes point-of-use loading RIDD1 with a therapeutic agent and inserting the loaded RIDD1 into the vagina. The method includes point-of-use loading RIDD2 with the therapeutic agent and replacing RIDD1 with RIDD2 in the vagina.

In an embodiment, the method includes delivering, with RIDD1, a therapeutically effective amount of the therapeutic agent to the vagina.

In an embodiment, the method includes delivering, with RIDD2, a therapeutically effective amount of the therapeutic agent to the vagina.

In an embodiment, the method includes point-of-use loading RIDD1 and RIDD2 with a lactic acid composition. The method includes delivering a therapeutically effective amount of lactic acid to the vagina.

In an embodiment, the method includes removing RIDD1 from the vagina and point-of-use reloading RIDD1 with the therapeutic agent.

In an embodiment, the method includes replacing RIDD2 with the reloaded RIDD1 in the vagina.

In an embodiment, the method includes comprising delivering, with the reloaded RIDD1, a therapeutically effective amount of the therapeutic agent to the vagina.

In an embodiment, the method includes replacing RIDD1 with RIDD2 in the vagina and delivering a therapeutically effective amount of the therapeutic agent from the RIDD2 to the vagina.

In an embodiment, the method includes repeating the POU-reloading, repeating the insertion/removal of the RIDDs to/from the vagina to provide continuous delivery of a therapeutically effective amount of the therapeutic agent for 1 day, or 1 week, or 1 month, or 2 months, or 3 months, or 4 months to 6 months, or 9 months to 12 months, or 18 months, or 24 months, or 36 months or more. In a further embodiment, the therapeutic agent is lactic acid.

The present disclosure provides another method. In an embodiment, a method for treating or preventing bacterial vaginosis (BV) is provided. The method includes inserting a POU-loaded RIDD1 into the vagina. The POU-loaded RIDD1 is POU-loaded or reloaded with a lactic acid composition. The method includes delivering, with RIDD1, a therapeutically effective amount of the lactic acid composition to maintain vaginal lactic acid concentration above 0.1%, and vaginal pH at or below (less than) pH 4.5. RIDD1 maintains this lactic acid concentration and pH at the area of epithelial surface immediately adjacent to the ring. The method further includes POU-loading RIDD2 with the lactic acid composition. The method includes replacing RIDD1 with POU-loaded RIDD2 in the vagina. The POU-loaded/reloaded RIDD2 continues to deliver, to the vagina, a therapeutically effective amount of the lactic acid and maintains vaginal lactic acid concentration above 0.1%, and vaginal pH at or below (less than) pH 4.5. RIDD2 maintains this lactic acid concentration and pH at the area of epithelial surface immediately adjacent to the ring.

In an embodiment, the method includes continuously replacing the POU-loaded RIDD (either RIDD1 or RIDD2) that is present in the vagina with a POU-reloaded RIDD (either RIDD1 or RIDD2), continuously delivering a therapeutically effective amount of the lactic acid to the vagina, and maintaining the vaginal lactic acid and pH as described above, for a period from 1 day, or 1 week, or 1 month, or 2 months, or 3 months, or 4 months to 6 months, or 9 months to 12 months, or 18 months, or 24 months, or 36 months (or any time duration therebetween) or more.

In an embodiment, the method continuously delivers 1 mg/day, or 10 mg/day, or 50 mg/day, or 200 mg/day to 500 mg/day, or 1000 mg/day, or 10,000 mg/day of lactic acid to the vagina for a period from 1 day, or 1 week, or 1 month, or 2 months, or 3 months, or 4 months to 6 months, or 9 months to 12 months, or 18 months, or 24 months, or 36 months, (or any time duration therebetween) or more.

The present system, device, and methods surprisingly overcome the problems with episodic treatment of BV and dramatically reduce (or eliminate) the recurrence of BV in women.

Conventional sustained release rings are cost-prohibitive or are unavailable in many regions of the world. Conventional factory loaded IDD rings, for example, must be disposable and therefore are relatively costly—especially for a person living in a resource-limited country. In addition to cost, it is also logistically impractical to deliver a steady supply of replacement factory-loaded IDD rings to persons in remote regions of many resource-limited countries—especially over an extended time period. Extended use IDD ring therapy—by way of conventional factory loaded IDD rings—therefore, is simply not a viable option to most people living in resource-limited countries.

The present POU load intravaginal delivery system, device, and method advantageously overcome the economic and supply obstacles blocking use of conventional factory loaded IDD rings in resource-limited countries. The present POU system is well-suited for use in resource-limited countries because the RIDDs are reusable—reducing product cost, reducing replacement cost, and reducing product delivery logistical obstacles. The present system with RIDDs and the POU recharge kit enables POU loading by the person living in a resource-limited country further reducing cost and supply issues. The RIDDs and the POU-recharge kit reduce the demand for replenishment product. In this way, the present system, device, and methods unexpectedly provide extended genital tract treatment to people everywhere—and especially to people in resource-limited countries. The present system surprisingly and unexpectedly provides a new approach—a new solution—for the treatment of genital tract infections to people in resource-limited countries, especially those suffering from BV, HIV, and/or STIs.

In addition, the present system streamlines the regulatory requirements of production because the present system avoids regulatory obstacles. Facilities that load drugs into controlled release devices must deal with the added complexity of complying with both medical device and drug regulations. The present system simplifies regulatory compliance.

6. Application

The system, device and/or methods of the present disclosure can be applied to prevent or treat one or more of the following genital tract ailments: bacterium such as *Chlamydia trachomatis, Neisseria gonorrhoeae, Gardnerella vaginalis, Porphyromonas levii, Prevotella bivia, Prevotella corporis, Anaerococcus prevotii, Fusobacterium nucleatum, Bacteroides ureolyticus, Micromonas micros, Propionibacterium acnes, Megasphaera elsdenii, Peptostreptococcus anaerobius Eggerthella lenta, Anaerococcus tetradius, Atopobium vaginae, Ureaplasma urealyticum, Mobiluncus curtisii, Mobiluncus mulieris, Mycoplasma hominis*; a virus such as herpes simplex virus type 1 (HSV-I), herpes simplex virus type 2 (HSV-2), *human papillomavirus* (HPV), or human immunodeficiency virus (HIV); a yeast or fungus such as *Candida albicans*; a protozoan such as *Trichomonas vaginalis* or any combination thereof. In an embodiment, one, or both, of the POU-loaded/reloaded RIDDs are self-administered by the end user to overcome the alkalinizing effect of semen on the vaginal environment.

DEFINITIONS

Any numerical range recited herein, includes all values from the lower value to the upper value, in increments of one unit, provided that there is a separation of at least 2 units between any lower value and any higher value. As an example, if it is stated that the amount of a component, or a value of a compositional is between 1 and 100, it is intended that all individual values, such as, 1, 2, 3, etc., and all subranges, such as, 1 to 20, 55 to 70, 197 to 100, etc., are expressly enumerated in this specification. For values that are less than one, one unit is considered to be 0.0001, 0.001, 0.01 or 0.1, as appropriate. These are only examples of what is specifically intended, and all possible combinations of numerical values between the lowest value and the highest value enumerated, are to be considered to be expressly stated in this application. In other words, any numerical range recited herein includes any value or subrange within the stated range.

The term "composition," as used herein, includes a mixture of materials that comprise the composition, as well as reaction products and decomposition products formed from the materials of the composition.

The term "comprising," and derivatives thereof, is not intended to exclude the presence of any additional component, step or procedure, whether or not the same is disclosed herein. In order to avoid any doubt, all compositions claimed herein through use of the term "comprising" may include any additional additive, adjuvant, or compound whether polymeric or otherwise, unless stated to the contrary. In contrast, the term, "consisting essentially of" excludes from the scope of any succeeding recitation any other component, step or procedure, excepting those that are not essential to operability. The term "consisting of" excludes any component, step or procedure not specifically delineated or listed. The term "or", unless stated otherwise, refers to the listed members individually as well as in any combination.

The term "controlled release" is the release of therapeutic agent gradually, or at a pre-determined rate, over a period of time.

The term "epithelial cell" is any cell or cells that line the inside cavities and lumen of the body of a subject including the genital tract.

The term "epithelial surface" is the surface or layer formed by epithelial cells.

The term "genital tract," as used herein, is any portion of the structures from the ovaries to the vulva in a female or from the testicles to the external urethral meatus in a male.

The term "polymer" is a macromolecular compound prepared by polymerizing monomers of the same or different type. "Polymer" includes homopolymers, copolymers, terpolymers, interpolymers, and so on.

The term "therapeutically effective amount," as used herein, is the amount of a material that is effective for producing a desired therapeutic effect.

The terms "treat" or "treatment" encompass prophylaxis, therapy and cure.

The term "permeability," as used herein, refers to the degree to which a material allows diffusion-mediated flux of a therapeutic agent across the material.

The term "vagina" is a portion of the female genital tract.

By way of example, and not limitation, examples of the present disclosure are provided.

EXAMPLES

Example 1

Load capacity for water swellable polyurethanes (PU) is evaluated. In this example, RIDDs are formed from a single PU material. The outer surface of the reservoir material does not restrict flux of the therapeutic agent and does not serve a metering function.

TABLE 1

Figure 8:
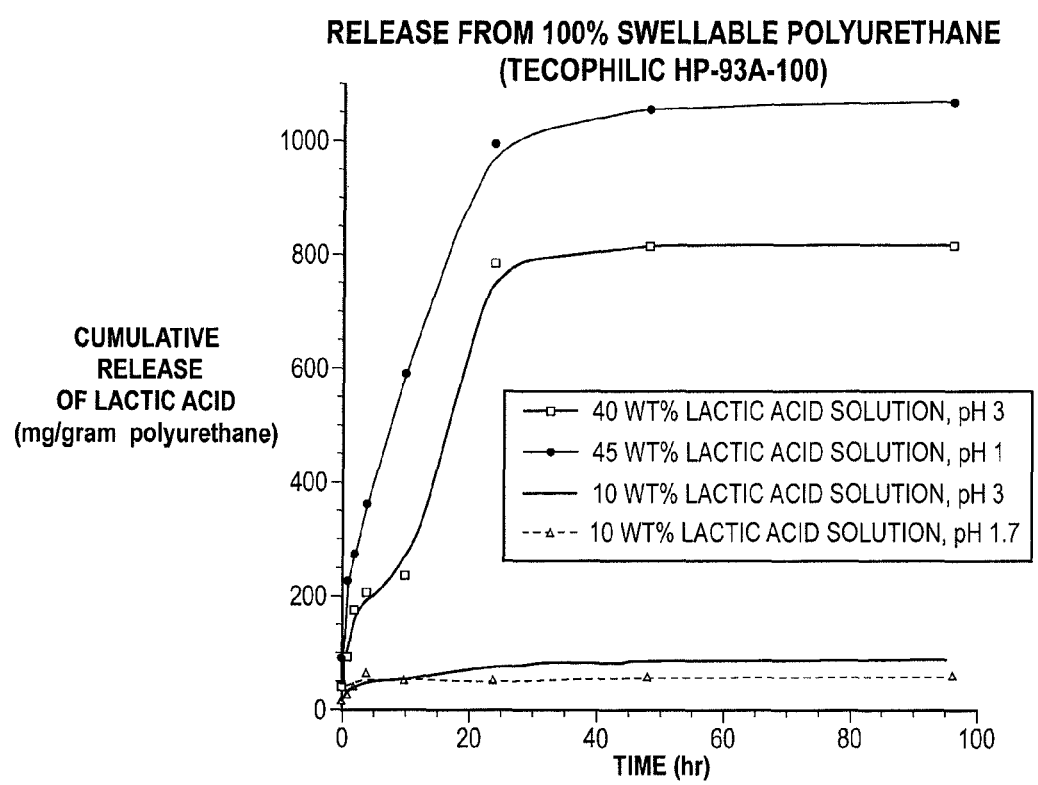
FIG. 8 is a graph showing the release of lactic acid over time from a polyurethane RIDD in accordance with an embodiment of the present disclosure.

| PU1 20% ws PU (Tecophilic HP-60D-20) | Device A, FIG. 6 |
| PU2 60% ws PU (Tecophilic HP-60D-60) | Device B, FIG. 7 |
| PU3 100% ws PU Tecophilic HP-93A-100) | Device C, FIG. 8 |

PU1-PU3—from Lubrizol Advanced Materials, Cleveland, OH, each PU is an aliphatic polyether polyurethane
ws—water swellability Each of PU1-PU3 is formed into segments of extruded rods to form respective Devices 1, 2, and 3 with the following dimensions: 8 mm diameter, 50 mm length, 3 grams in weight.

Devices A, B, and C are loaded by soaking, for 7 days in 25 mL solution of each lactic acid solution shown in Table 2 below. The pH of solutions 2 and 4 is raised to pH 3 by addition of sodium hydroxide to pH 1 lactic acid solution. The results are shown in FIGS. 6, 7, and 8.

TABLE 2

| Solution | Lactic acid (LA) aqueous solution |
|---|---|
| 1 | 10 wt % LA, pH 1.7 |
| 2 | 10 wt % LA, pH 3 |
| 3 | 45 wt % LA, pH 1 |
| 4 | 40 wt % LA, pH 3 |

Lactic acid is L-lactic acid (PURAC PF 90)

FIGS. 6, 7, and 8 each show the cumulative lactic acid released per gram of respective PU1, PU2, and PU3 when the lactic acid loaded Devices A, B, and C are subsequently immersed in 40 mL of 40 mM citrate buffer, pH 4.0, with daily changes of the buffer to maintain sink conditions.

Lactic acid release rates of up to 1000 mg per gram of polyurethane are observed with the most water swellable polyurethane. A broad range of release rates (from 15 mg/gram/day to 1000 mg/gram/day) can be obtained by varying polyurethane type, and the concentration and pH of lactic acid used for loading. As disclosed above, these materials allow a wide range of loading and release rates, and very high upper limits of loading and release. The data shows that the degree of polyurethane water swellability correlates with the degree of uptake and release of the lactic acid. Lactic acid, like water, has a high capability for hydrogen bonding to PU1, PU2, and PU3, which are hydrophilic PUs.

The high loading and release levels seen with some of the above devices and conditions may be useful for certain applications. However, when configured as above, without the addition of a different material as the outer layer, (i.e., without a permeable wall with a lower permeability than the enclosed polymer constituting the reservoir portion of the device), the release rate is initially very rapid, but soon slows, and departs substantially from linearity in less than 12 hours.

Example 2

When more constant release rates are desired, the RIDD can be a two layer structure wherein the inner layer is the reservoir material and the outer layer is the permeable wall. The permeable wall has a lower permeability to the therapeutic agent than does the reservoir material.

RIDDs with a permeable wall serving a metering function are constructed as follows.

An inner reservoir portion is fabricated by injection molding PU2 (Tecophilic HP-60D-60 resin) into a toroid-shaped ring. The PU2 resin is vacuum dried 4 hours at 150° F., and injection molded by a screw extruder into a two piece vented aluminum mold, forming a ring of 42 mm outside diameter and 5.8 mm cross sectional diameter and with a weight of 3.7 grams. The ring is subsequently coated to form the permeable wall by dipping in a solution of Tecoflex EG-85A in tetrahydrofuran. Multiple cycles of dipping and rotation assure even coating of the dipping solution. The dipped ring is then oven dried at 150° F. for two hours to adhere the permeable wall to the inner reservoir portion.

The dipping cycle is varied to produce RIVRs with a permeable wall having a thickness in the range from 0.002 inches to 0.013 inches and as shown by RIVRs D-G in Table 3.

RIVR with a silicone permeable wall is fabricated by dip-coating a 42 mm×5.8 mm ring injection molded from PU2 (Tecophilic HP-60D-60 resin). The RIVR is coated with two cycles of dipping in room temperature vulcanization (RTV) silicone dispersion (NuSil MED-6605, NuSil Silicone Technology LLC) and oven dried at 150° F. for two hours after each dipping cycle. This process produces a RIVR with a silicone permeable wall having a thickness of 0.004 inches as shown by RIVR H in Table 3.

TABLE 3

| RIVR | Permeable Wall | Permeable Wall Thickness Inches (mm) |
| --- | --- | --- |
| D | PU--Tecoflex EG-85A | 0.0025 (0.064) |
| E | PU--Tecoflex EG-85A | 0.0050 (0.127) |
| F | PU--Tecoflex EG-85A | 0.0075 (0.190) |
| G | PU--Tecoflex EG-85A | 0.013 (0.33) |
| H | Silicone--Nusil MED-6605 | 0.004 (0.102) |

Reservoir material is PU2

RIVRs D-H are loaded with L-lactic acid (PURAC PF 90) as follows:

Each RIVR D-H is immersed in 40 mL of lactic acid (L-lactic acid solution of 45%, at pH 1, or L-lactic acid 40% neutralized to pH 3 with 10 N sodium hydroxide).

The RIVRs D-H are soaked at room temperature for 7 days without stirring, and then rinsed for 30 seconds under running tap water. To test the rate of lactic acid release each RIVR D-H is immersed in 100 mL of elution buffer (citrate buffer pH 4, or citrate/phosphate buffer pH 3, 5, or 6), and incubated at 37° C. without stirring. Sample buffer is removed and replaced daily to maintain sink conditions, and the concentration of L-lactic acid in samples determined by enzymatic assay (R-Biopharm, Darmstadt, Germany).

Figure 9A:
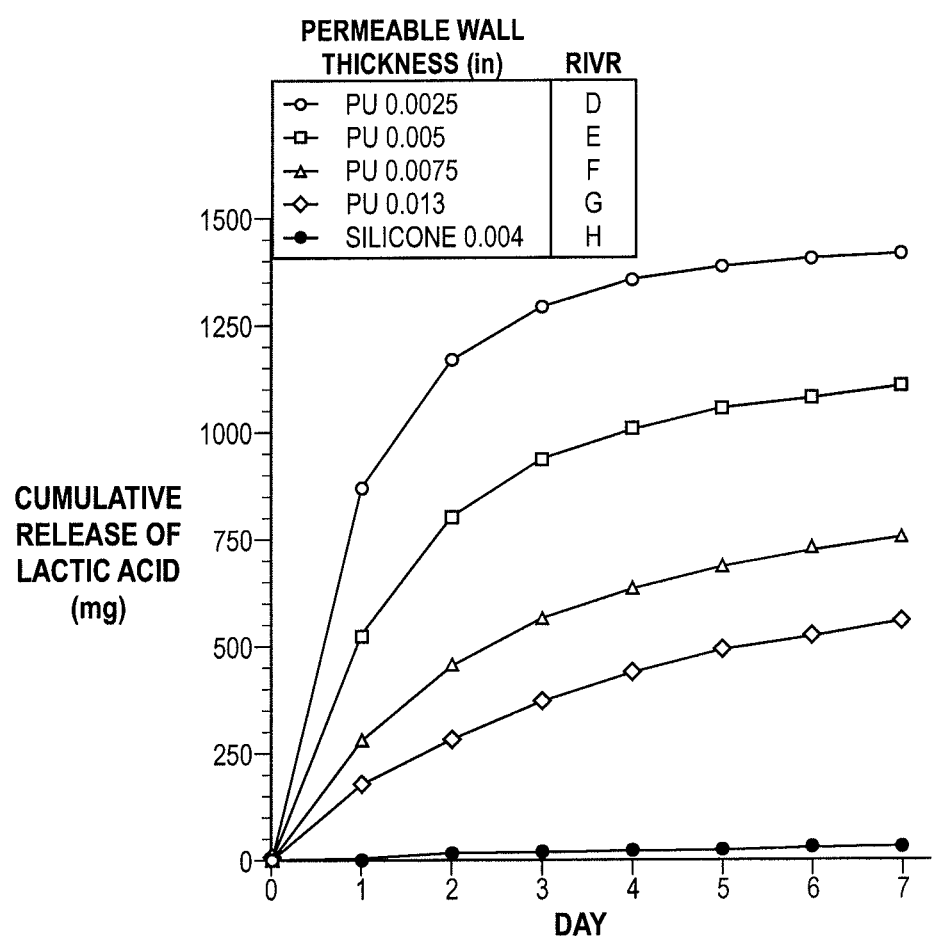
FIG. 9A is a graph showing the cumulative release of lactic acid from a RIVR in accordance with an embodiment of the present disclosure.
Figure 9B:
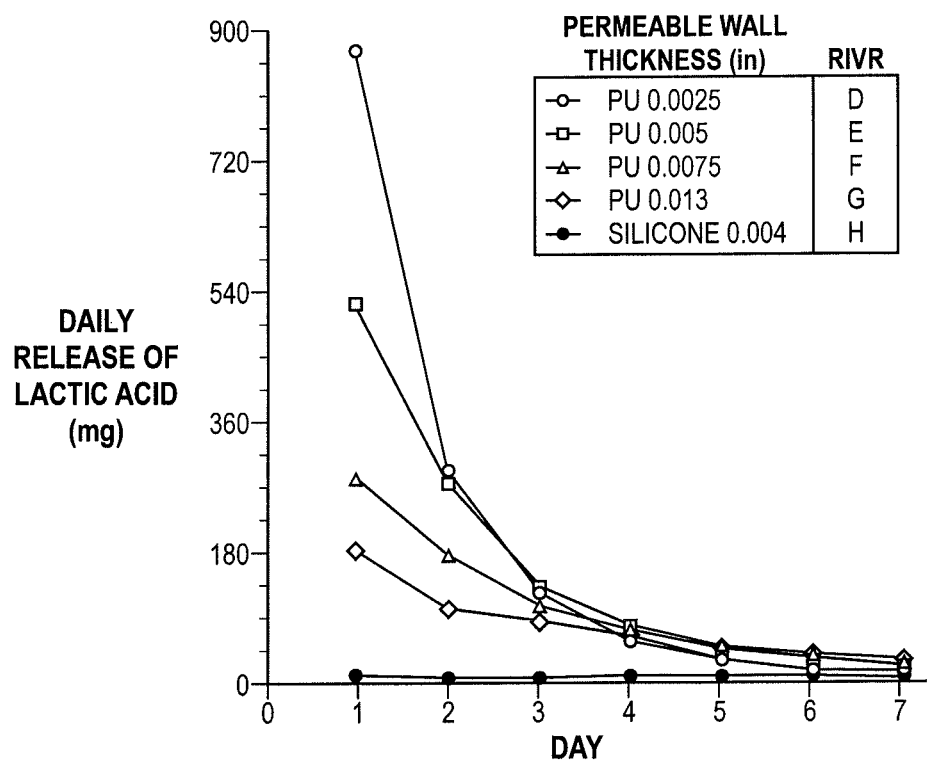
FIG. 9B is a graph showing the daily release of lactic acid from a RIVR in accordance with an embodiment of the present disclosure.

FIGS. 9A and 9B—load conditions: immersion of the RIVR in 40 ml of 45 wt % lactic acid solution at pH 1.

Compare FIG. 7 to FIG. 9A. Device B (FIG. 7) and RIVRs D-H (FIG. 9A) are made of the same reservoir material, PU2. FIG. 9 shows that RIVRs D-H with a permeable wall provide sustained release when compared to Device B.

FIG. 9 shows that the permeable wall slows lactic acid release substantially compared to that shown in FIG. 7 with the same Tecophilic HP-60D-60 reservoir material. For example, compare Device B (FIG. 7) and RIVR F (FIG. 9) soaked in the same lactic acid solution (45% L-lactic acid, pH 1). RIVR F provides prolonged release, with 39% of its total lactic acid still being released between day 3 and day 7, whereas Device B releases nearly 100% of its total lactic acid within two days as demonstrated by the flattening of the release curve in FIG. 7.

Figure 10:
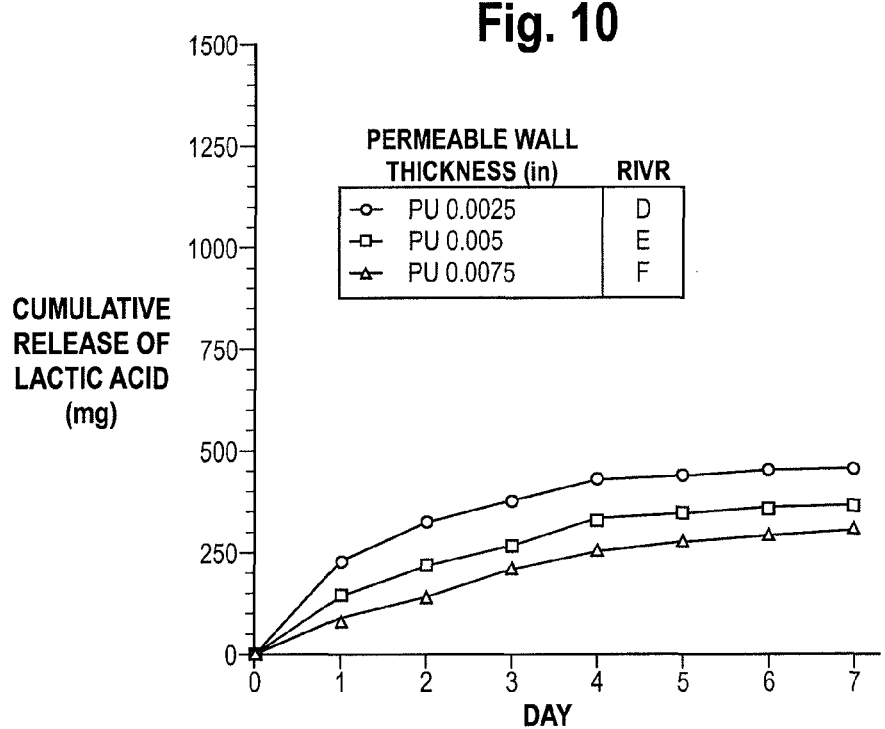
FIG. 10 is a graph showing the cumulative release of lactic acid from a RIVR in accordance with an embodiment of the present disclosure.

FIG. 10 load conditions: immerse RIVR in 40 ml 40 wt % lactic acid at pH 3. FIG. 10 shows that increasing the pH of the lactic acid loading solution to pH 3 decreases the loading and release rates substantially compared to loading at pH 1 (FIG. 9), providing an additional means to customize these rates.

The curves for RIVRs D-H (permeable wall EG-85A polyurethane) in FIGS. 9 and 10 follow exponential decay in the reduction of rate of release over time.

Figure 11:
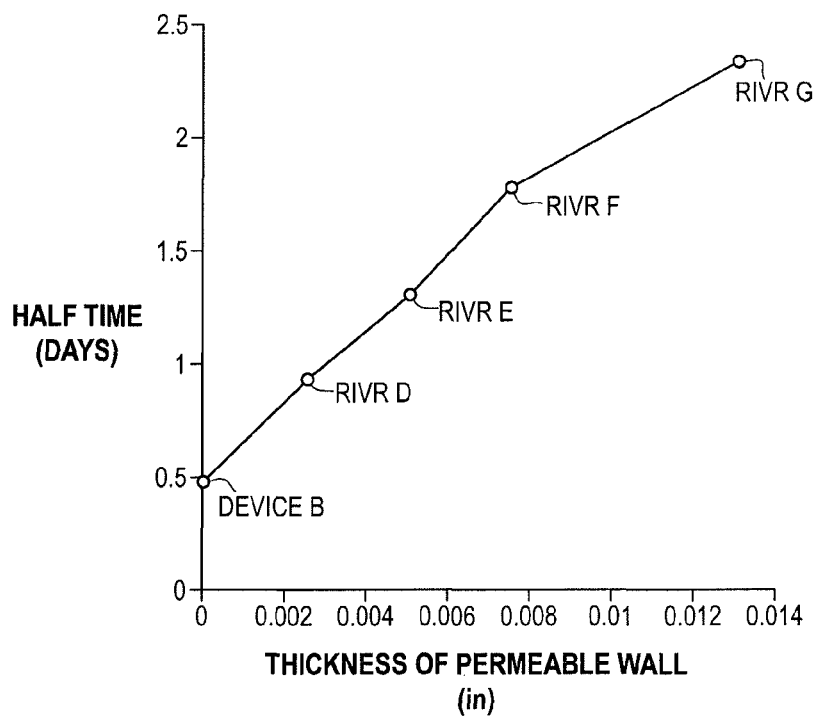
FIG. 11 is a graph showing the relationship between the half time of lactic acid release and the permeable wall thickness for RIVRs in accordance with an embodiment of the present disclosure.

FIG. 11 plots half times for lactic acid release (determined from the curves in FIG. 9 with RIVRs loaded with 45% L-lactic acid at pH 1) against the thickness of the permeable wall of the RIVRs. FIG. 11 shows that the release half time increases linearly as the thickness of the permeable wall is increased.

The release profile of the RIVR H with the silicone permeable wall (filled triangles) is also shown in FIGS. 9A and 9B. The silicone permeable wall has a lower permeability than the EG-85A polyurethane permeable wall of the other RIVR D-G. The release rate for RIVR H is low, and the curve is very flat, with near constant release of about 4 mg/day over the 7 day period.

Since the low permeability of the silicone permeable wall results in low a release rate, the charged reservoir is only minimally depleted during the release period. Thus, the lactic acid concentration gradient remains nearly constant, resulting in a near constant release rate over the release period. The silicone permeable wall also reduces the rate of loading of the reservoir portion of the RIVR, but because of the high concentration of lactic acid used for loading, the permeable wall's resistance to loading is overcome, and a substantial amount of lactic acid enters the reservoir. Thus, surprisingly, by combining loading a therapeutic agent provided at high concentration in the recharging fluid, with a low permeability permeable wall, the POU-load/-reload method is capable of providing constant release rate over many days. This is a constancy of release previously only achieved by sustained release devices with stores of therapeutic agent prepositioned in the reservoir in insoluble form, and which would not have been expected to be achieved with a diffusion-load RIDD.

Figure 12:
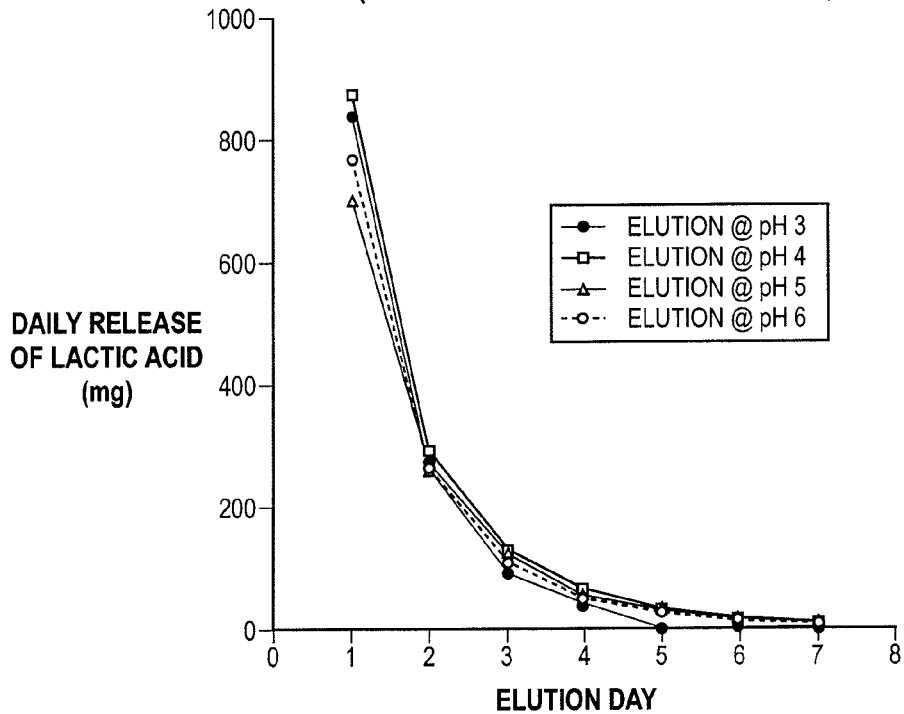
FIG. 12 is a graph showing the release of lactic acid over time from RIVRs when eluted in buffers of different pH in accordance with an embodiment of the present disclosure.

FIG. 12 (RIVR D) shows that the rate of release of lactic acid is minimally affected by the pH of the eluting buffer. This is surprising in light of the fact that load/reload is strongly dependent on the pH of the lactic acid in the recharging fluid (compare FIGS. 9 and 10). FIG. 12 indicates that the release of lactic acid from RIVRs in the vagina will not be influenced by vaginal pH, which can vary over a wide range, from approximately pH 3 to pH 6. Lactic acid release from the present RIVRs will follow predicable release rates regardless of the unpredictable vaginal pH.

The two-layer design (reservoir material encased in a permeable wall) combines the advantages of high loading capability (due to the high uptake capabilities of the reservoir polymer), and a relatively constant release rate over prolonged periods (due to the metering effect of the permeable wall, with greater thicknesses of the permeable wall extending the duration of release). Although the lower permeability of the permeable wall also reduces the speed of POU-load/-reload with therapeutic agent in the recharging vessel, adequately rapid loading can be achieved by providing a relatively high concentration of therapeutic agent (or bulk therapeutic agent) in the POU-recharge kit.

The rate of load/reload (recharging) of a RIDD is dependent on the flux of the lactic acid or other therapeutic agent entering the RIDD from the surrounding therapeutic agent. The flux is proportional to the concentration gradient between the surrounding therapeutic agent and the interior of the RIDD. Since the concentration in the therapeutic agent can be varied over a wide margin, the present POU system can be adjusted so that the time required for POU-reloading a RIDD is equal to the desired wear time of the RIDD. This enables a simple method of reuse and replacement of the RIDDs by a woman. A pair of RIDDs can be POU-loaded and POU-reloaded many times by the woman. One of the RIDDs can be alternately worn inside the body and while the other RIDD is reloaded or recharged outside the body by immersing the expended RIDD in a solution of the therapeutic agent in the recharge vessel. At the appropriate interval, the woman replaces the RIDD in the vagina with the recharged RIDD in the recharge vessel. This process is repeated as long as administration of the RIDDs is desired. The therapeutic agent present in the recharge vessel (in solution or other form) is refreshed (replaced) at the time of RIDD exchange.

Devices A-C and RIVRs D-H are solid and are permeable to the therapeutic agent, with which they load by passive diffusion rather than by convection, advection, capillary action, or other bulk flow mechanisms, as might be the means of fluid and therapeutic agent entry into macroporous devices, for example sponges or fibrous tampon-like devices. The devices A-C and RIVRs D-H are solid devices rather than macroporous devices. In devices A-C and RIVRs D-H, the spaces between polymer chains are too small to allow entry of microorganisms (typically larger than 100 nanometers), yet large enough to allow entry of the therapeutic agent, which will generally have molecular weights of a few hundred to a few tens-of-thousands, and hydrodynamic radii on a nanometer scale. Devices A-C and RIVRs D-H can be rapidly loaded with substantial quantities of a therapeutic agent by diffusion-load-reload. The absence of macroporosity in the present RIDDs advantageously reduces colonization by bacteria and other microorganisms, and improves cleanability.

Example 3

Many therapeutic agents are more stable in dry form than in solution. Thus the therapeutic agent can be provided in tablet, capsule, film, or powder form. Moreover, provision in dry form can be more compact, thus reducing bulk and weight in comparison to solutions. In this example, a kit is provided comprising two RIVRs, a recharge vessel, and a bulk supply of water-soluble therapeutic agent in tablet form. The end user fills the recharge vessel to a fill mark with water, drops in the required number of tablets or other solid dosage form, and mixes the water and tablet until the tablet is dissolved. The first RIVR is placed in contact with the solution of the therapeutic agent thus formed, and incubated at room temperature for the requisite loading time. The first RIVR is removed, rinsed in water, and inserted into the vagina. While the first RIVR is worn, the recharge vessel is similarly prepared and the second RIVR is similarly loaded. The first RIVR is removed from the vagina and the second RIVR is inserted in the vagina. The first RIVR is then reloaded by contact with a solution of the therapeutic agent in the recharge vessel. The process is repeated as needed for the desired duration of treatment or prophylaxis. A suitable antimicrobial preservative may be included in the tablet or in the dissolving liquid to prevent microbial growth during the loading incubation.

Example 4

In addition to use for delivery of hydrophilic therapeutic agents such as lactic acid, RIDDs can also be used for point-of-use charging and recharging for sustained release of hydrophobic agents, or agents with characteristics intermediate between hydrophilic and hydrophobic agents. For example, the hydrophobic therapeutic agent dapivirine is released from a RIDD with a non-water swellable reservoir made with Tecoflex EG-85A, and an outer permeable wall made of hydrophilic polyurethane such as Tecophilic HD-60D-20. Alternatively, the permeable wall can be made of a mixture of Tecoflex EG-85A and Tecophilic HD-60D-20. The dapivirine is applied to the RIDD by dusting the RIDD with a fine powder of the drug substance and incubating the coated RIDD in the recharge vessel, then rinsing off external drug with water, or with a solvent. Alternatively, to achieve solubilization of dapivirine in a fluid contacting the RIDD in a point-of-use recharge vessel, a suitable solvent such as a vegetable oil can be used. The dapivirine or other hydrophobic therapeutic agent can provide premixed in the oil, or mixed at the point-of-use by dissolving a tablet or capsule containing the therapeutic agent.

Example 5

In order to reduce the stiffness of the RIVR for easier vaginal insertion, and to prevent bowing during compression the RIVR may have an oval cross section or other shape with height greater than width. A RIVR is fabricated with a mold adapted to provide an oval or rounded rectangular cross section with a cross sectional height and width of 6.2 mm×3.7 mm, corner radii of 1.85 mm, and overall outside diameter of 56 mm. The RIVR is easily compressed for vaginal insertion, and does not bow or twist on compression.

Use of the present POU system is illustrated for a woman in a resource limited country (such as a less developed country), who is at risk for BV and for frequent recurrences of BV based on past episodes or by being a member of a community or geographic region known to have a high BV prevalence. When such a woman has BV, she is at increased risk for acquiring HIV, and multiple STIs should she be exposed to them by a sexual partner. The woman obtains the POU load intravaginal delivery system for sustained vaginal release of L-lactic acid. The woman receives the POU recharge kit with two RIDDs, a container of bulk lactic acid solution and a recharge vessel. Two RIDDs are provided, each RIDD is a RIVR with a 60 mm outside diameter and 6.5 mm×3.8 mm oval cross section. Each RIVR will fit nearly all women without need for medical examination or fitting. Each of the two RIVRs is small enough for easy insertion, and large enough to be well retained, and easily grasped and retrieved by means of a finger inserted into the vagina. Before using RIVR1, the woman POU-loads RIVR1 by placing RIVR1 in the recharge vessel with enough liquid therapeutic agent (lactic acid solution) to cover the RIVR1. RIVR1 is allowed to diffusion-load for one week, and then is rinsed with several changes of water in the recharge vessel, then removed, washed with additional water, and inserted into the vagina. The second RIVR (RIVR2) is POU-loaded by placement thereof in the recharge vessel by the woman. The woman immerses RIVR2 with fresh lactic acid solution for one week, while RIVR1 is being worn in the vagina. After one week, the woman rinses RIVR2 in the recharge vessel and further rinses it with water. She removes RIVR1 from the vagina, and replaces it with the POU-loaded RIVR2. She cleans RIVR1 and POU-loads RIVR1 in the recharge vessel to be reloaded over the week that RIVR2 will be present in the vagina. Each week, the cycle of removal, cleaning, and recharging is repeated, with the two rings being repeatedly exchanged between the vagina and the recharge vessel. This can be repeated for many cycles with a single pair of RIVRs, the POU-recharge kit, and a bulk container of liquid L-lactic therapeutic agent.

Example 6

Figure 13:
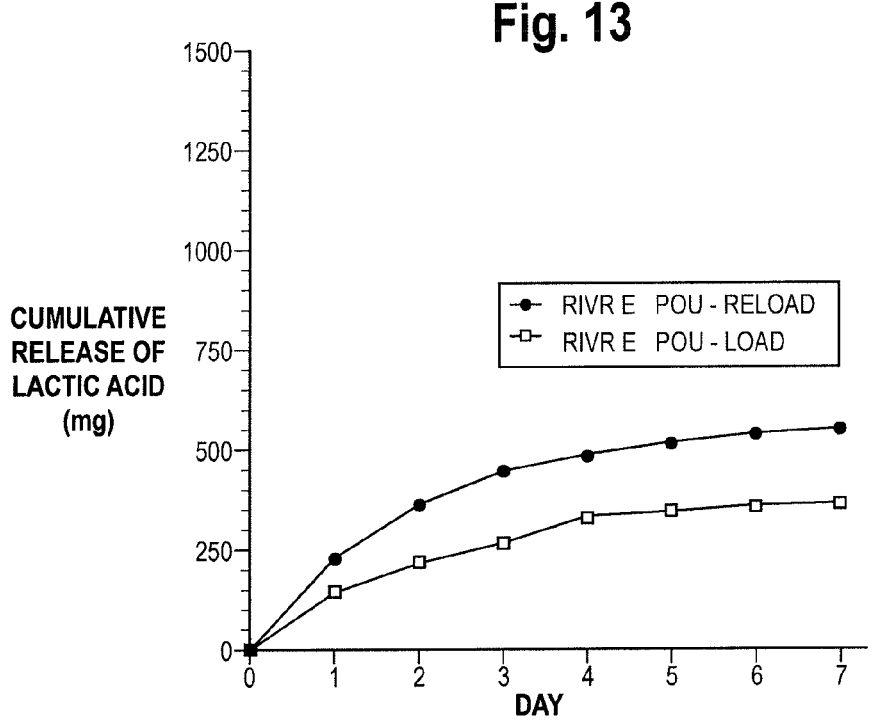
FIG. 13 is a graph showing the release of lactic acid over time from a RIVR that is POU-loaded and subsequently POU-reloaded in accordance with an embodiment of the present disclosure.

In FIG. 13, RIVR E (from Table 2, permeable wall—0.0050 inches thick) is diffusion-loaded by soaking 7 days in a recharge vessel containing 40 wt % lactic acid pH 3. The RIVR E is then eluted 7 days in 40 ml 40 mM citrate buffer solution pH 4 to simulate the pH of the vaginal cavity. Thereafter, RIVR E is reloaded by soaking 7 days in the recharge vessel in 40 wt % lactic acid, pH 3, and again eluted 7 days in 40 ml 40 mM citrate buffer pH 4. This sequence demonstrates that cycling POU-load and POU-reload RIVRs from the vagina to the recharging vessel provides continuous delivery of a therapeutic agent by recharging and replacing the RIVRs repeatedly.

FIG. 13 plots the cumulative release during elution of the POU-loaded RIVR E (closed circles) and the POU-reloaded RIVR E (open squares). The plot of the closed circles in FIG. 13 is the same plot of the open circles of FIG. 10. The two plots in FIG. 13 show that repeated POU-loading and unloading of the RIVR E can be performed, with similar elution profiles, thus enabling sustained release over multiple cycles by repeated exchange of one RIVR being soaked for 7 days and second RIVR simultaneously being worn vaginally for 7 days.

It is specifically intended that the present disclosure not be limited to the embodiments and illustrations contained herein, but include modified forms of those embodiments including portions of the embodiments and combinations of elements of different embodiments as come within the scope of the following claims.

What is claimed is:

1. A point-of-use load intravaginal delivery system comprising:
    a first reusable intravaginal delivery device (RIDD1) and a second reusable intravaginal delivery device (RIDD2), each RIDD comprising a permeable wall defining an enclosed interior reservoir, the reservoir adapted to receive a therapeutic agent; and
    a point-of-use recharge kit comprising a therapeutic agent, the point-of-use recharge kit for point-of-use loading at least one of the RIDDs with the therapeutic agent.

2. The system of claim 1 wherein each RIDD is a diffusion-loaded RIDD.

3. The system of claim 1 wherein the permeable wall is composed of a material selected from the group consisting of a polyurethane and a silicone.

4. The system of claim 1 wherein the therapeutic agent is a lactic acid composition.

5. The system of claim 1 wherein the point-of-use recharge kit comprises a bulk amount of the therapeutic agent selected from the group consisting of a powder and a solution.

6. The system of claim 1 wherein the point-of-use recharge kit further comprises a member selected from the group consisting of a recharge vessel, a cleaning solution, a cleaning device, and combinations thereof.

7. The system of claim 6 wherein the RIDD1 is in a vagina and the RIDD2 is in operative communication with a component of the point-of-use recharge kit.

8. The system of claim 1 wherein the therapeutic agent is a lactic acid composition; and each RIDD has an intravaginal lactic acid release rate from 1 mg/day to 10,000 mg/day for 1 to 30 days.

9. The system of claim 4 wherein the lactic acid composition is in RIDD1 and RIDD1 is located in a vagina.

10. The system of claim 9 wherein the point-of-use recharge kit comprises a recharge vessel; and the recharge vessel contains RIDD2 immersed in an amount of the lactic acid composition.

11. A method for delivering a therapeutic agent to a vagina, the method comprising:
    providing a point-of-use recharge kit comprising a first reusable intravaginal delivery device (RIDD1), a second RIDD (RIDD2) and a therapeutic agent, each RIDD comprising a permeable wall defining an enclosed interior reservoir, each RIDD adapted to receive the therapeutic agent; and
    enabling, with the kit, point-of-use loading of the therapeutic agent to at least one RIDD.

12. The method of claim 11 comprising inserting RIDD1 in the vagina;
    delivering a therapeutically effective amount of the therapeutic agent to the vagina with RIDD1; and
    point-of-use loading RIDD2 with the therapeutic agent.

13. The method of claim 12 comprising removing the RIDD1 from the vagina;
    inserting the RIDD2 into the vagina; and
    further delivering, with point-of-use loaded RIDD2, a therapeutically effective amount of the therapeutic agent into the vagina.

14. A method for delivering a therapeutic agent to a vagina, the method comprising:
    point-of-use loading a first reusable intravaginal delivery device (RIDD1) with a therapeutic agent;
    inserting the loaded RIDD1 into the vagina;
    point-of-use loading a second RIDD (RIDD2) with the therapeutic agent;
    replacing RIDD1 with RIDD2 in the vagina.

15. The method of claim 14 comprising delivering, with RIDD1, a therapeutically effective amount of the therapeutic agent to the vagina.

16. The method of claim 14 comprising delivering, with RIDD2, a therapeutically effective amount of the therapeutic agent to the vagina.

17. The method of claim 14 comprising point-of-use loading RIDD1 and RIDD2 with a lactic acid composition.

18. The method of claim 14 comprising removing RIDD1 from the vagina and point-of-use reloading RIDD1 with the therapeutic agent.

19. The method of claim 18 comprising replacing RIDD2 with the reloaded RIDD1 in the vagina.

20. The method of claim 19 comprising delivering, with the reloaded RIDD1, a therapeutically effective amount of the therapeutic agent to the vagina.

* * * * *